US007273730B2

(12) United States Patent
Du Breuil Lastrucci

(10) Patent No.: US 7,273,730 B2
(45) Date of Patent: Sep. 25, 2007

(54) NESTED PCR EMPLOYING DEGRADABLE PRIMERS

(75) Inventor: Rusla M. Du Breuil Lastrucci, Huntsville, AL (US)

(73) Assignee: Invitrogen Corporation, Carlsbad, CA (US)

( * ) Notice: Subject to any disclaimer, the term of this patent is extended or adjusted under 35 U.S.C. 154(b) by 569 days.

(21) Appl. No.: 10/445,097

(22) Filed: May 27, 2003

(65) Prior Publication Data

US 2003/0228620 A1 Dec. 11, 2003

Related U.S. Application Data

(60) Provisional application No. 60/382,578, filed on May 24, 2002.

(51) Int. Cl.
C12P 19/34 (2006.01)
C12Q 1/68 (2006.01)
(52) U.S. Cl. .......................... 435/91.2; 435/6
(58) Field of Classification Search ............ 435/6, 435/91.2
See application file for complete search history.

(56) References Cited

U.S. PATENT DOCUMENTS

| | | |
|---|---|---|
| 4,582,788 A | 4/1986 | Erlich |
| 4,663,290 A | 5/1987 | Weis et al. |
| 4,683,195 A | 7/1987 | Mullis et al. |
| 4,683,202 A | 7/1987 | Mullis |
| 4,889,818 A | 12/1989 | Gelfand et al. |
| 4,965,188 A | 10/1990 | Mullis et al. |
| 5,035,996 A | 7/1991 | Hartley |
| 5,137,814 A | 8/1992 | Rashtchian et al. |
| 5,229,283 A | 7/1993 | Berninger |
| 5,314,809 A | 5/1994 | Erlich et al. |
| 5,334,515 A | 8/1994 | Rashtchian et al. |
| 5,340,728 A | 8/1994 | Grosz et al. |
| 5,348,853 A | 9/1994 | Wang et al. |
| 5,374,553 A | 12/1994 | Gelfand et al. |
| 5,418,149 A | 5/1995 | Gelfand et al. |
| 5,556,773 A | 9/1996 | Yourno |
| 5,668,005 A | 9/1997 | Kotewicz et al. |
| 5,683,896 A | 11/1997 | Hartley et al. |
| 5,853,980 A * | 12/1998 | Rollin et al. .................. 435/5 |
| 5,866,336 A | 2/1999 | Nazarenko et al. |
| 5,945,313 A | 8/1999 | Hartley et al. |
| 6,063,608 A | 5/2000 | Kotewicz et al. |
| 6,287,823 B1 | 9/2001 | Hartley |

FOREIGN PATENT DOCUMENTS

| | | |
|---|---|---|
| EP | 0 050 424 A1 | 4/1982 |
| EP | 0 084 796 A2 | 8/1983 |
| EP | 0 201 184 A2 | 12/1986 |
| EP | 0 237 362 A1 | 9/1987 |
| EP | 0 258 017 A2 | 3/1988 |
| WO | WO96/10640 A1 | 4/1996 |

OTHER PUBLICATIONS

Akins, R.A., et al., "Mitochondrial Plasmids of Neurospora: Integration into Mitochondrial DNA and Evidence for Reverse Transcription in Mitochondria," *Cell* 47:505-516, Cell Press (1986).

Alexander, F., et al., "Proteolytic Processing of Avian Sarcoma and Leukosis Viruses *pol-endo* Recombinant Proteins Reveals Another *pol* Gene Domain," *J. Virol.* 61:534-542, American Society for Microbiology (1987).

Amersham Pharmacia Biotech, "Drop-In/drop-Out Nested PCR," 1 page, available at http://autodna.apbiotech.com/handbook/mut/mu4-20.htm, (updated Feb. 7, 2000).

Barr, P.J., et al., "Expression of Active Human Immunodeficiency Virus Reverse Transcriptase in *Saccharomyces cerevisiae*," *Bio/Tech.* 5:486-489, Nature Publishing Company (1987).

Berg, J., et al., "Rapid-Cycle PCR in Temporarily Compartmentalized Capillaries: Two-Round PCR in a Single Capillary Prevents Product Carry-Over," *BioTech.* 29:680-683, Eaton Publishing Company (2000).

Berg, J., et al., "Single-tube two-round polymerase chain reaction using the LightCycler™ instrument," *J. Clin. Virol.* 20:71-75, Elsevier Science B.V. (Jan. 2001).

Duncan, B.K., "DNA Glycosylases," in: *The Enzymes*, Boyer, P.D., ed., Academic Press, New York, NY, pp. 565-586 (1981).

Farmerie, W.G., et al., "Expression and Processing of the AIDS Virus Reverse Transcriptase in *Escherichia coli*," *Science* 236:305-308, American Association for the Advancement of Science (1987).

Fawcett, D.H., et al., "Transposable Elements Controlling I-R Hybrid Dysgenesis in D. melanogaster Are Similar to Mammalian LINEs," *Cell* 47:1007-1015, Cell Press (1986).

Gerard, G.F., et al., "Influence on Stability in *Escherichia coli* of the Carboxy-Terminal Structure of Cloned Moloney Murine Leukemia Virus Reverse Transcriptase," *DNA* 5:271-279, Mary Ann Liebert, Inc., Publishers (1986).

Grace, M.B., et al., "Degradable dUMP Outer Primers in Merged Tandem (M/T)-Nested PCR: Low- and Single-Copy DNA Target Amplification," *Anal. Biochem.* 263:85-92, Academic Press (1998).

Grandgenett, D.P., et al., "A Single Subunit from Avian Myeloblastosis Virus with Both RNA-Directed DNA Polymerase and Ribonuclease H Activity," *Proc. Natl. Acad. Sci. USA* 70:230-234, National Academy of Sciences (1973).

(Continued)

*Primary Examiner*—Kenneth R. Horlick

(57) ABSTRACT

The invention is directed to one-tube nested nucleic acid amplification methods, as well as compositions for performing these methods, which employ one or more outer primers containing one or more exo-sample nucleotides and inner primers. Nested amplification reactions are performed in these methods in the presence of an agent that degrades the exo-sample-nucleotide-containing primers in time course fashion during the PCR cycles.

12 Claims, 8 Drawing Sheets

OTHER PUBLICATIONS

Hansen, J., et al., "RNase H Activity Associated with Bacterially Expressed Reverse Transcriptase of Human T-cell Lymphotropic Virus III/ Lymphadenopathy-associated Virus," *J. Biol. Chem.* 262:12393-12396, The American Society for Biochemistry and Molecular Biology (1987).

Holland, P.M., et al., "Detection of specific polymerase chain reaction product by utilizing the 5'→3' exonuclease activity of *Thermus aquaticus*," *Proc. Natl. Acad. Sci. USA* 88:7276-7280, National Academy of Sciences (1991).

Hu, Y., "A Single Tube Nested PCR for Detection of *Shigella spp*," *Poster abstract* presented at the 2001 FDA Science Forum, (Jan. 2001).

Kotewicz, M.L., et al., "Cloning and overexpression of Moloney murine leukemia virus reverse transcriptase in *Escherichia coli*," *Gene* 35:249-258, Elsevier Science Publishers (1985).

Krokan, H.E., et al., "DNA glycosylases in the base excision repair of DNA," *Biochem. J.* 325:1-16, The Biochemical Society/Portland Press (1997).

Larder, B., et al., "AIDS virus reverse transcriptase defined by high level expression in *Escherichia coli*," *EMBO J.* 6:3133-3137, IRL Press Ltd. (1987).

Lee, L.G., et al., "Allelic discrimination by nick-translation PCR with fluorogenic probes," *Nucl. Acids Res.* 21:3761-3766, Oxford University Press (1993).

Life Technologies, "Uracil DNA Glycosylase," available online at http://order.lifetech.com/flow.icl?sku=18054015 &orderidentifier=ID9924603136564F154, (available Jun. 2001).

Loh, E.Y., et al., "Polymerase Chain Reaction with Single-Sided Specificity: Analysis of T Cell Receptor δ Chain," *Science* 243:217-220, American Association for the Advancement of Science (1989).

Michel, F. and Lang, B.F., "Mitochondrial class II introns encode proteins related to the reverse transcriptases of retroviruses," *Nature* 316:641-643, Macmillan Publishers (1985).

Mullis, K., et al., "Specific Enzymatic Amplification of DNA In Vitro: The Polymerase Chain Reaction," *Cold Spring Harbor Symp. Quant. Biol.* 51:263-273, Cold Spring Harbor Laboratory (1986).

Nazarenko, I.A., et al., "A closed tube format for amplification and detection of DNA based on energy transfer," *Nucl Acids Res.* 25:2516-2521, Oxford University Press (1997).

Pecharatana, S., et al., "Genotyping Ocular Strains of *Chlamydia trachomatis* by Single-tube Nested PCR," *PCR Meth. Appl.* 3:200-204, Cold Spring Harbor Laboratory Press (1993).

Pierre, J. and Laval, J., "Specific Nicking of DNA at Apurinic Sites by Peptides Containing Aromatic Residues," *J. Biol. Chem.* 256:10217-10220, The American Society of Molecular Biology and Biochemistry (1981).

Rice, N.R., et al., "The *gag* and *pol* Genes of Bovine Leukemia Virus: Nucleotide Sequence and Analysis," *Virol.* 142:357-377, Academic Press (1985).

Roche, "Uracil-DNA Glycosylase," Roche Catalog, Cat. Nos. 1 269 062 and 1 444 646, 2 pages (1999).

Roche, "Uracil-DNA Glycosylase, heat-labile," Roche Catalog, Cat. Nos. 1 775 367 and 1 775 375, 2 pages (2000).

Roche, "Uracil-DNA Glycosylase," Roche Catalog, Cat. Nos. 1 269 062 and 1 444 646, 2 pages (Jun. 2001).

Roche, "Uracil-DNA Glycosylase, heat-labile," Roche Catalog, Cat. Nos. 1 775 367 and 1 775 375, 2 pages (May 2001).

Roth, M.J., et al., "Purification and Characterization of Murine Retroviral Reverse Transcriptase Expressed in *Escherichia coli*," *J. Biol. Chem.* 260:9326-9335, The American Society of Biological Chemists, Inc. (1985).

Saiki, R.K., et al., "Enzymatic Amplification of β-Globin Genomic Sequences and Restriction Site Analysis for Diagnosis of Sickle Cell Anemia," *Science* 230:1350-1354, American Association for the Advancement of Science (1985).

Saiki, R.K., et al., "Primer-Directed Enzymatic Amplification of DNA with a Thermostable DNA Polymerase," *Science* 239:487-491, American Association for the Advancement of Science (1988).

Sandigursky, M. and Franklin, W.A., "Uracil-DNA Glycosylase in the Extreme Thermophile *Archaeoglobus fulgidus*," *J. Biol. Chem.* 275:19146-19149, The American Society for Biochemistry and Molecular Biology, Inc. (2000).

Schaaper, R.M., et al., "Infidelity of DNA synthesis associated with bypass of apurinic sites," *Proc. Natl. Acad. Sci. USA* 80:487-491, National Academy of Sciences (1983).

Schwartz, D.E., et al., "Nucleotide Sequence of Rous Sarcoma Virus," *Cell* 32:853-869, Cell Press (1983).

Seiki, M., et al., "Human adult T-cell leukemia virus: Complete nucleotide sequence of the provirus genome integrated in leukemia cell DNA," *Proc. Natl. Acad. Sci. USA* 80:3618-3622, National Academy of Sciences (1983).

Shinnick, T.M., et al., "Nucleotide sequence of Moloney murine leukaemia virus," *Nature* 293:543-548, Macmillan Publishers (1981).

Sonigo, P., et al., "Nucleotide Sequence of Mason-Pfizer Monkey Virus: An Immunosuppressive D-Type Retrovirus," *Cell* 45:375-385, Cell Press (1986).

Sun, B., et al., "Studies on the Catalytic Mechanism of Five DNA Glycosylases," *J. Biol. Chem.* 270:19501-19508, The American Society for Biochemistry and Molecular Biology, Inc. (1995).

Takatsuji, H., et al., "Expression of cauliflower mosaic virus reverse transcriptase in yeast," *Nature* 319:240-243, Macmillan Publishers (1986).

Tanese, N., et al., "Expression of Reverse Transcriptase Activity of Human T-Lymphocyte Virus Type III (HTLV-III/LAV) in *Escherichia coli*," *J. Virol.* 59:743-745, American Society for Microbiology (1986).

Tanese, N., et al., "Expression of enzymatically active reverse transcriptase in *Escherichia coli*," *Proc. Natl. Acad. Sci. USA* 82:4944-4948, National Academy of Sciences (1985).

Toh, H., et al., "Sequence homology between retroviral reverse transcriptase and putative polymerases of hepatitis B virus and cauliflower mosaic virus," *Nature* 305:827-829, Macmillan Publishers (1983).

Toh, H., et al., "Close structural resemblance between putative polymerase of a *Drosophila* transposable genetic element 17.6 and *pol* gene product of Moloney murine leukaemia virus," *EMBO J.* 4:1267-1272, IRL Press Ltd. (1985).

Tyagi, S. and Kramer, F.R., "Molecular Beacons: Probes that Flouresce upon Hybridization," *Nature Biotech.* 14:303-308, Nature America Publishing (1996).

Wang, Y., et al., "Rapid Sizing of Short Tandem Repeat Alleles Using Capillary Array Electrophoresis and Energy-Transfer Fluorescent Primers," *Anal. Chem.* 67:1197-1203, American Chemical Society (1995).

Wittwer, C.T., et al., "The LightCycler™:A Microvolume Multisample Fluorimeter with Rapid Temperature Control," *BioTech.* 22:176-181, Eaton Publishing Company (1997).

Yuki, S., et al., "Identification of genes for reverse transcriptase-like enzymes in two *Drosophila* retrotransposons, 412 and *gypsy*, a rapid detection method of reverse transcriptase genes using YXDD box probes," *Nucl. Acids Res.* 14:3017-3030, IRL Press Ltd. (1986).

International Search Report for International Patent Application No. PCT/US03/16634, mailed Dec. 1, 2003, European Patent Office, Netherlands.

\* cited by examiner ered herein by reference.

BACKGROUND OF THE INVENTION

1. Field of the Invention

The present invention relates to the fields of molecular biology and molecular diagnostics. The present invention provides improved methods and compositions for amplification of nucleic acids. In particular, the invention includes materials and methods for the amplification and/or detection of target nucleic acid sequences by nested PCR.

2. Related Art

PCR amplifies specific nucleic acid sequences through a series of manipulations including denaturation, annealing of oligonucleotide primers, and extension of the primers with DNA polymerase (see U.S. Pat. No. 4,683,202, U.S. Pat. No. 4,683,195, EP 201,184, EP 050,424, EP 084,796, EP 258,017, EP 237,362, U.S. Pat. No. 4,582,788, U.S. Pat. No. 4,683,202, Mullis, K. B. et al. Cold Spring Harbor *Symp. Quant. Biol.* 51:263 (1986), Saiki, R. et al. *Science* 230:1350 (1985), Saiki, R. et al. *Science* 231:487 (1988), and Loh, E. Y. et al. *Science* 243:217 (1988)). These steps can be repeated many times, potentially resulting in large amplification of the number of copies of the original specific sequence.

Although PCR has the potential to permit enormous amplification of a desired specific sequence, it can also enormously amplify a non-desired sequence for various reasons including mis-annealing of the primers and contamination of the input sample. The contamination problem is particularly severe in laboratories where PCR is heavily used, such as diagnostic laboratories. The basic rule when performing any PCR is that the products generated post-amplification should be kept spatially separated from the targets or reagents to be used in any subsequent PCR reactions. If this is not strictly adhered to, contamination and false positives of all the following PCR reactions are likely to occur. Contamination by the carryover of amplification products from a previous PCR reaction may be due to aerosol formation or contamination of work-surfaces, reagents, pipettes etc. Using separate work areas and sample handling equipment for product handling versus setup and using the enzyme uracil DNA glycosylase (UDG), as described below, can keep this contamination to a minimum.

To prevent carryover from previously amplified PCR reactions in subsequent PCR reactions, several preventive measures have been suggested. One such measure involves substituting dUTP for dTTP in the PCR reaction to generate deoxyuridine containing PCR products. Although the triphosphate form of deoxyuridine, dUTP, is present in living organisms as a metabolic intermediate, it is rarely incorporated into DNA. When dUTP is incorporated into DNA, the resulting deoxyuridine is promptly removed in vivo by normal processes, e.g. processes involving UDG. Both single- and double-stranded DNAs that contain uracil are substrates for UDG. UDG cleaves the N-glycosyl bond between the uracil base and the phosphodiester backbone of DNA. The resulting apyrimidinic DNA molecule becomes susceptible to hydrolysis at high temperatures. Further, the apyrimidinic site in the DNA blocks DNA polymerase from using the DNA strand as a template for the synthesis of a complementary DNA strand (Schaaper, R. et al. *Proc. Natl. Acad. Sci. USA* 80:487 (1983)). The presence of substantial numbers of apyrimidinic sites in each DNA target molecule interferes with further amplification procedures which use DNA polymerases to amplify target DNA.

To prevent contamination by carryover of reaction products, a sample would be treated with UDG prior to the a PCR reaction to destroy all uracil-containing contaminants. Methods utilizing UDG to prevent carryover and to decrease contamination in standard PCR reactions have been addressed in U.S. Pat. Nos. 5,683,896, 6,287,823, 5,945,313, 5,035,996, 5,229,283, and 5,137,814. All of these methods employ exo-sample nucleotides in combination with a treatment, such as a glycosylase treatment, to overcome the problem of contamination.

In addition to contamination problems, PCR based methodologies also frequently are not sufficiently sensitive to allow target amplification when the target is a rare sequence. The detection of a rare sequence in a sample is limited by the amount of amplified product available to be tested. Rare sequences can be overlooked in conventional analytical practices.

The need for improved sensitivity and specificity in PCR reactions designed to amplify rare sequences is addressed in U.S. Pat. No. 4,683,195, which describes the use of nested primers for increasing sensitivity of single copy genes. According to the method, two pairs of primers are used to amplify first a larger template nucleic acid molecule and, subsequently, a target nucleic acid sequence that is contained in the amplified template molecule. For many research applications (specifically those working with low or poor quality target or rare messages), applying two rounds of PCR markedly enhances the specificity and sensitivity of PCR analysis.

With reference to FIG. 1, classical nested PCR uses two sets or pairs of amplification primers. A first pair of primers-termed the outer primers-are designed to amplify a template nucleic acid molecule as in standard PCR. After amplification of the template, an aliquot from the amplification reaction mixture is typically diluted into a second amplification reaction mixture. The second amplification reaction mixture contains a second set of primers-termed the inner primers-designed to anneal to an internal portion of the template and to amplify a target nucleic acid sequence from the template molecule. The amplification product of the second reaction is, by definition, shorter than the first.

Nested PCR is designed to increase the sensitivity of PCR by directly re-amplifying the product from the outer primer PCR reaction-amplified template-with a second PCR reaction designed to amplify a specific target nucleic acid sequence within the template nucleic acid molecule. Another advantage of nested PCR is its increased specificity, since the inner, nested primers anneal only if the amplified product resulting from the outer primers has the corresponding, specific sequences, i.e., if the proper template has been amplified.

A very distinct PCR product is normally obtained in nested PCR. The profound improvement in amplification efficiency is believed to be attributed to the increased specificity provided by the use of two primer pairs, the large total number of cycles possible and the replenishment of reaction components such as Taq DNA polymerase.

The chance of amplifying non-desired sequences is reduced with nested PCR as compared to regular PCR since non-desired sequences amplified in the first amplification reaction are not likely to contain a sequence to which the primers for the second amplification reaction-the inner primers-will bind. In contrast, performing the same total number of cycles (30 to 40) with either set of primers individually often amplifies non-desired sequences.

A number of variations of nested PCR are known to those skilled in the art. One commonly used variation is semi-nested PCR. In a semi-nested PCR reaction, one inner primer is included in the primary amplification reaction. In certain applications, semi-nested PCR will add enough specificity for a desired targeted PCR product.

Two step reaction protocols for nested PCR have several drawbacks.

First, the presence of the outer primer pair in the second PCR reaction may result in non-specific amplification of undesired sequences or reduced amplification of the target sequence by the inner primers. An additional drawback is the potential for contamination in the samples when the tubes from the first PCR reaction are opened to remove an aliquot to be used for the second PCR reaction.

The possibility of contamination represents a significant problem with classical nested PCR. After completion of the first amplification reaction, the PCR tube must be opened, the amplification reaction mixture diluted, and then an aliquot of the first amplification reaction mixture must be transferred to a second tube for a second amplification reaction. The tube for the second amplification reaction will typically include the components for the second reaction including the inner primers as inner primers are not typically included in the first amplification reaction. The sample handling and the proximity of the amplification product of a first amplification reaction to the reagents used in a second amplification reaction both contribute to an increased risk of contamination of the second amplification reaction. Another disadvantage with this technique is the cost involved in doing two rounds of PCR reactions.

A number of single-tube nested PCR methods have been developed to try to overcome the difficulties associated with classical nested PCR. Some of these methods rely on having the second PCR mixture physically separated from the first reaction mixture, for example, by a mineral oil layer. After the first round of amplification, the two solutions are mixed by centrifugation and then the second PCR reaction begins. Because an oil layer is required, the benefit of using heated-lid thermocyclers, where there normally is no need for an oil layer, is lost. One example of a single-tube, nested PCR protocol that relies on a physical separation of the reaction components is found in U.S. Pat. No. 5,556,773. This patent discloses physically separating the inner primers from the first amplification reaction mixture and, after the first reaction, introducing the inner primers by centrifugation.

U.S. Pat. No. 5,314,809 describes drop-in/drop-out nested PCR, a method that utilizes an inner primer pair having a lower annealing temperature than the outer primer pair resulting in the inner primers not being extended during the first amplification. The drop-in/drop-out one tube nested PCR technique requires that primers be specifically designed to provide inner and outer primer pairs with sufficient differences in annealing temperatures to practice the technique. The inner primers must have a low annealing temperature to prevent them from annealing to the template during the PCR reaction of the outer primer pair. Although, this technique circumvents the addition of an oil layer to separate the reagents of the two separate reactions and the need to mix the two layers after the first reaction, the restrictions imposed on primer annealing temperatures can make it difficult to suitable primer pairs.

Another method that utilizes specially designed primer pairs is disclosed in U.S. Pat. No. 5,340,728. This patent discloses manipulating the primer concentration and annealing times according to a kinetic model in order to optimize amplification of the target nucleic acid sequence.

Each of the methods designed to improve upon nested PCR has its own attendant deficiencies. Some require specialized materials and/or are limited by complicated primer selection criteria and reaction conditions that reduce the general applicability of the methods. There remains a need in the art for simplified methods for increasing both the specificity and sensitivity of nested PCR amplification. Improved methods are desirable that also eliminate processing steps, minimize cross contamination, and subsequent inaccurate results. These and other needs are met by the present invention.

BRIEF SUMMARY OF THE INVENTION

The present invention provides, in part, improved methods and compositions for nucleic acid amplification. The novel methods provided offer, in part, enhanced target specificity and sensitivity over prior methods. Methods of the invention are particularly useful for amplification and detection of target nucleic acid sequences by the polymerase chain reaction (PCR) with an increase in sensitivity, target specificity, and/or a decrease in cross-sample contamination. The invention further includes compositions for performing the methods of the invention (e.g., reaction mixtures) and compositions comprising amplification products produced by the methods of the invention.

In some embodiments, the present invention provides a composition, comprising a template nucleic acid molecule comprising a target nucleic acid sequence and at least one exo-sample-nucleotide-containing primer capable of annealing to the template at a specific nucleotide sequence in the template.

Compositions preferably contain at least one nucleotide polymerase enzyme and may also contain at least one agent capable of degrading an exo-sample nucleotide. In some embodiments, compositions of the invention do not contain amplified template. In some embodiments, a composition of the invention may contain a primer capable of annealing to the template at a nucleotide sequence located 3' to the nucleotide sequence to which the exo-sample-nucleotide-containing primer anneals to the template.

In some embodiments, the present invention provides a composition comprising one or more exo-sample-nucleotide-degrading agents, one or more polymerases, one or more nucleoside triposphates, and one or more primers comprising at least one exo-sample nucleotide. In some embodiments, compositions of this type do not contain amplified nucleic acid. In some embodiments, on or more exo-sample-nucleotide-degrading agents may be an enzyme, for example, a DNA glycosylase. Suitable DNA glycosylases include, but are not limited to uracil-DNA glycosylases (UGDs/UNGs), UNG1, TAG, alkA, MAG, MAG1, N-methyl-purine glycosylase, EndoIII, EndoVIII, EndoIX, NTG1, NTH, hydroxy-methyl-DNA glycosylase, formyluracil-DNA glycosylase, 2,6-dihydroxy-5N-formamiodopyrimidine DNA glycosylase, OGG1, OGG2, S3, PDG, and 5-methyl-cytosine-DNA glycosylase. In some embodiments, one or more DNA glycosylases may be thermostable. A thermostable glycosylase may retain at least 5% of the original glycosylase activity after heating to 95° C. for 30 minutes. Polymerases of the compositions of the invention may be DNA polymerases and may be thermostable polymerases or both. A thermostable DNA polymerase may retain at least 5% of the original polymerase activity after heating to 95° C. for 30 minutes.

In some embodiments, the present invention provides a method for amplifying one or more target nucleic acid sequences present in one or more template nucleic acid molecules in an amplification reaction. The method may include mixing one or more templates with an amplification reaction mixture that may include one or more outer and/or inner primers or primer pairs. Each primer in an outer primer pair may comprise a sequence with sufficient complementarity to a portion of a template to anneal to the template in an amplification reaction. In some embodiments, either or both members of an outer primer pair may contain one or more (e.g., 1, 2, 3, 4, 5, 6, 7, 8, 9, 10, etc.) exo-sample nucleotides.

In some embodiments, each inner primer and/or each member of an inner primer pair may comprise a sequence with sufficient complementarity to a portion of a template to anneal to the template in an amplification reaction. The portion of the template to which each inner primer anneals may completely or partially overlap or may be between the portions of the template to which the corresponding outer primers anneal.

A target nucleic acid sequence is preferably located in the template nucleic acid molecule such that extension of either or both of the inner primers results in incorporation into the primer extension product a sequence corresponding to the target sequence. Target nucleic acid sequences may be between the portions of the template to which the inner primers anneal. The reaction mixture may further comprise one or more agents capable of cleaving an exo-sample nucleotide, for example, a DNA glycosylase enzyme.

The present invention is also directed to a composition comprising one or more (e.g., 1, 2, 3, 4, 5, etc.) of the following components: one or more nucleic acid template molecules, one or more agents that cleave nucleic acids at exo-sample nucleotides, one or more polymerases, one or more nucleoside triposphates (e.g., one or more deoxyribonucleoside triphosphates such as dUTP, dCTP, dATP, dGTP, dTTP, dITP, etc.), one or more inner primers, or one or more outer primers, wherein at least one outer primer comprises an exo-sample nucleotide. In some embodiments, the present invention provides a composition including a template nucleic acid molecule comprising a target nucleic acid sequence; an exo-sample-nucleotide-containing primer capable of annealing to the template at a specific nucleotide sequence in the template, a nucleotide polymerase enzyme and an agent capable of degrading an exo-sample nucleotide. Preferably, such compositions will not contain amplified template. In some embodiments, compositions of the present invention may further contain a primer capable of annealing to the template at a nucleotide sequence located 3' to the nucleotide sequence to which the exo-sample-nucleotide-containing primer anneals to the template.

In addition, the invention is also directed to a kit comprising instructions for performing nested polymerase chain reaction in which the relative concentration of one or more primers decreases with respect to one or more other primers during amplification of a target nucleic acid molecule. A kit of the present invention may include one or more of the following components in various combinations, or alternatively, as individual components: one or more sets of instructions for using the kit components and/or for performing one or more methods of the invention, one or more glycosylases, one or more buffers, one or more nucleoside triphosphates, one or more polymerases, one or more templates, one or more containers containing water, magnesium chloride or one or more solutions or buffers containing magnesium chloride, one or more polymerases with one or more antibodies, one or more single stranded nucleic acid binding proteins, and one or more primers (e.g., one or more inner primers and/or one or more outer primers containing one or more exo-sample nucleotides, etc.).

DETAILED DESCRIPTION OF THE INVENTION

Figure 1:
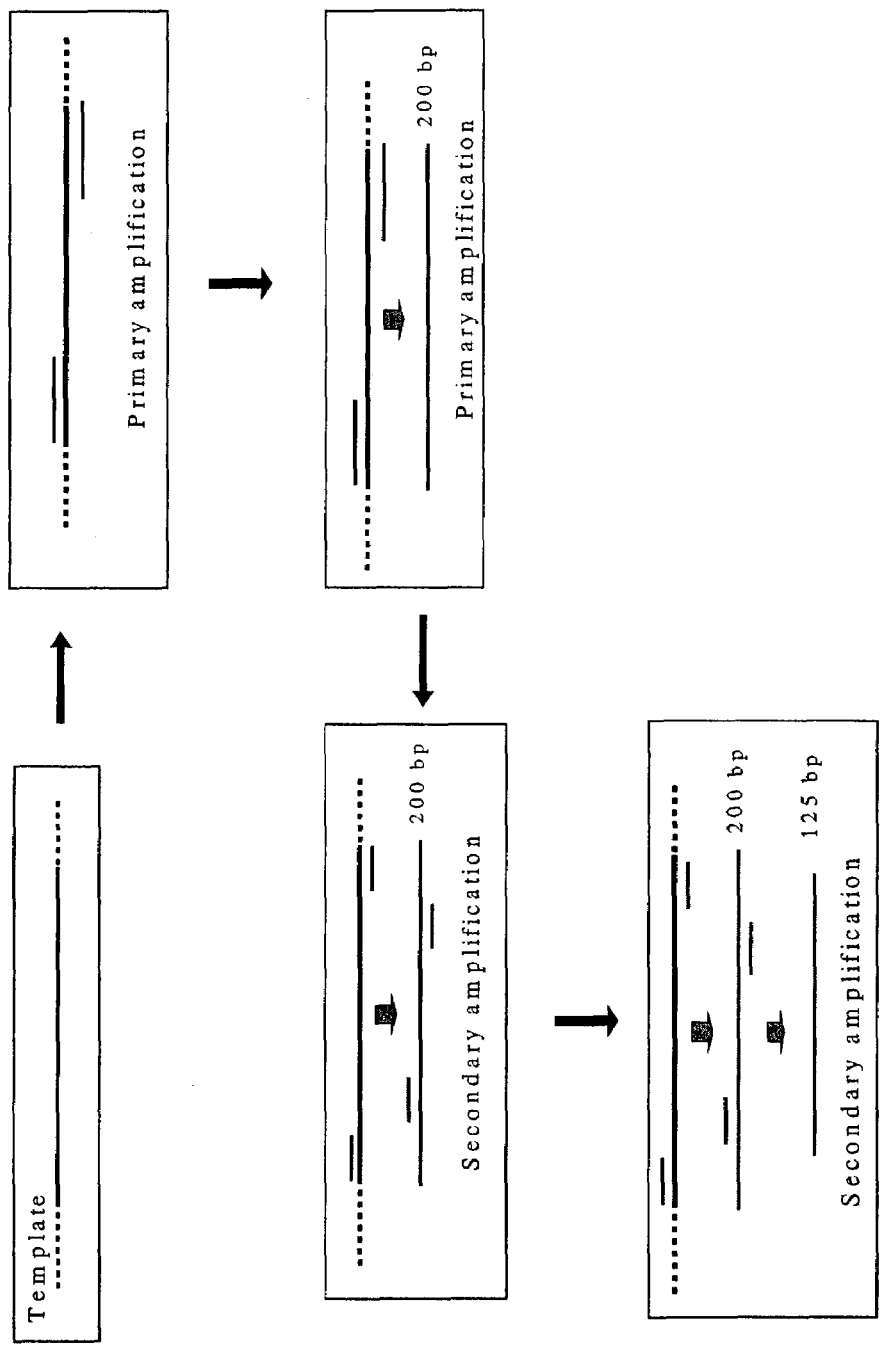
FIG. 1. Schematic drawing of a nested PCR process.

The invention provides, in part, methods for the nested amplification of target nucleic acid sequences present in template nucleic acid molecules. More specifically, the invention provides, in part, methods for nested PCR of a target nucleic acid sequence, wherein at least three (e.g., three, four, five, six, seven, eight, nine, ten, etc.) primers, which in most instances differ in nucleotide sequence, are used in amplification reactions. Typically, at least one of the primers will contain at least one (e.g., three, four, five, six, seven, eight, nine, ten, eleven, twelve, etc.) exo-sample nucleotide. Further, in many instances, these exo-sample nucleotides, in combination with an agent that degrades exo-sample nucleotides, will be used to alter the concentration of functional primers during an amplification reaction. For example, exo-sample nucleotides can be used, in conjunction with an agent or conditions where primers which contain these exo-sample nucleotides are rendered non-functional for purposes of becoming involved in amplification reactions, to decrease the concentration of primers which are capable of functioning in amplification reactions in a time course fashion. The invention further includes compositions (e.g., reaction mixtures and individual components of these reaction mixtures) for performing methods of the invention, as well products produced using methods of the invention (e.g., nucleic acid molecules which are produced using amplification methods of the invention).

Definitions

In the description that follows, a number of terms used in molecular biology and nucleic acid amplification technology are extensively utilized. In order to provide a clearer and consistent understanding of the specification and claims, including the scope to be given such terms, the following definitions are provided.

The term "amplification" is used herein to refer to any in vitro process for exponentially increasing the number of copies of a nucleotide sequence or sequences. Nucleic acid amplification results in the incorporation of nucleotides-ribonucleotides or deoxyribonucleotides-into primers to form DNA or RNA polynucleotides complementary to a template nucleic acid molecule. As used herein, one amplification reaction may consist of many rounds of primer extension. For example, one PCR reaction may consist of several cycles of denaturation and extension ranging from about 5 cycles to 1000 cycles, or more.

As will be understood by those of ordinary skill in the art, the methods of the invention allow the exponential amplification of a target nucleic acid sequence while reducing or eliminating the exponential amplification undesired nucleic acid sequences but may not prevent linear amplification.

Linear amplification does not usually represent a substantial problem in amplification procedures. For example, a single product molecule that contaminates a reaction through 20 cycles of PCR will result in only about 20 molecules if amplified linearly. However, this molecule could result in up to about a million molecules if amplified exponentially at maximal theoretical efficiency. Thus, linear amplification is generally inconsequential.

The presence of the amplified nucleic acid can be detected by any number of methods known in the art. One method of detection is to differentiate reaction products of a specific size by means of molecular weight. Methods for molecular weight differentiation may include gel filtration, sedimentation velocity, osmotic pressure, or gel electrophoresis, etc. The amplified nucleic acid can also be sequenced using other methods also known in the art.

Other methods of detecting the presence of amplified nucleic acid may include, but are not limited to, the use of labeling the nucleotides with a physical label capable of generating a detectable signal. The various "signal generating compounds" (labels) contemplated include radiolabels, chromogens, catalysts such as enzymes, luminescent compounds such as fluorescein and rhodamine, chemiluminescent compounds, radioactive elements, and direct visual labels. Useful labels include, but are not limited to, $^{32}P$, fluorescent dyes, colored or fluorescent proteins, electron-dense reagents, enzymes (as commonly used in ELISAs), biotin, digoxygenin, and haptens and proteins for which antisera or monoclonal antibodies are available. Examples of enzymes include, but are not limited to, alkaline phosphatase, horseradish peroxidase, luciferase, beta-galactosidase, etc. The selection of a particular label is not critical, but it will be capable of producing a signal either by itself or in conjunction with one or more additional substances.

The phrase "target nucleic acid sequence" is used herein to refer to any series of contiguous nucleotides in a template nucleic acid molecule (such as DNA, cDNA or RNA) to be amplified. One specific target nucleic acid sequence is a segment, region, or fragment of a nucleic acid molecule that hybridizes to at least one inner primer during a nested PCR reaction.

The term "nucleotide" is used herein to refer to a base-sugar-phosphate combination. Nucleotides are the monomeric units of nucleic acid polymers, e.g. DNA or RNA. The term includes ribonucleoside triphosphates, such as rATP, rCTP, rGTP, or rUTP, and deoxy-ribonucleotide triphosphates, such as dATP, dCTP, dUTP, dGTP, or dTTP. A "nucleoside" is a base-sugar combination, e.g. a nucleotide lacking phosphate. It is recognized in the art that there is certain interchangeability in usage of the terms nucleoside and nucleotide. For example, the nucleotide deoxyuridine triphosphate, dUTP, is a deoxyribonucleoside triphosphate. After incorporation into DNA, it serves as a DNA monomer, formally being deoxy-uridylate, i.e. dUMP or deoxyuridine monophosphate. One may say that one incorporates dUTP into DNA even though there is no dUTP moiety in the resultant DNA. Similarly, one may say that one incorporates deoxyuridine into DNA even though that is only a part of the substrate molecule.

The phrase "exo-sample nucleotide" is used herein to refer to a nucleotide that is generally not found in substantial amounts in the sample or nucleic acid molecule to be amplified unless deliberately introduced by methods known to those of skill in the art. A "substantial amount" is more than 3% of total nucleotides present in a sample or nucleic acid molecule unless deliberately incorporated into the nucleic acid sample, for example, by using the methods of the present invention.

The presence of deoxyuridine, or any other exo-sample nucleotide, may be determined readily using methods well known in the art. Other exo-sample nucleotides may include, but are not limited to, bromodeoxyuridine, 7-methylguanine, 5,6-dihydro-5,6-dihydroxydeoxythymidine, 3-methyldeoxa-denosine, inosine, 5-bromo-deoxycitidine, 5-methyl-deoxy-citidine, 5-bromo-deoxyuridine, O-6-methyl-deoxygua-nosine, 5-iodo-deoxyuridine, 8-oxy-deoxyguanine, ethanoadenine, 5,6-dihydrouracil, etc. (see Duncan, B. K., The Enzymes XIV: 565-586 (1981)). Any exo-sample nucleotide, which may be incorporated into nucleic acid molecules during an amplification reaction, may be used in this invention. Other exo-sample nucleotides may be envisioned by those of ordinary skill in the art and are within the scope of the invention.

The term "glycosylase" is used herein to refer to an enzyme that cleaves a glycosyl group from a molecule. One type of glycosylase, for example, is a DNA glycosylase. DNA glycosylases cleave the N-glycosyl bond between the target base and deoxyribose releasing a free base and leaving an apurinic/apyrimidinic (AP) site. Examples of DNA glycosylases may include, but are not limited to, uracil-DNA glycosylases (UDG/UNG) such as viral, bacterial, plant and human UNGs and *Saccharomyces cerevisiae* UNG1. Glycosylase includes akylbase-DNA glycosylases such as *Escherichia coli* TAG and alkA, *Saccharomyces cerevsiae* 3-methyladenine DNA glycosylase gene (MAG), *Saccharomyces pombe* MAG1, rodent/human N-methyl purine glycosylases (MPG) and *Arabidopsis thaliana* MPG. Also included are DNA glycosylases removing oxidized pyrimidines (EndoIII-like) such as *Escherichia coli* EndoIII, EndoVIII, and EndoIX, *Saccharomyces cerevisiae* NTG1 (a *Saccharomyces* homolog of Endo III), *Schizosaccharomyces pombe* NTH, human/bovine EndoIII homologue, mouse/bovine hydroxy-methyl-DNA glycosylase, and human formyluracil-DNA glycosylase. Other glycosylases included are DNA glycosylases removing oxidized purines such as *Escherichia coli* 2,6-dihydroxy-5N-formamiodopyrimidine (Fapy) DNA glycosylase (FPG), *Saccharomyces cerevisiae* 8-oxoguanosine DNA glycosylases 1 and 2 (OGG1 and OGG2), and *Drosophila melanogaster* S3. Glycosylases also include pyrimidine-dimer DNA glycosylases such as PDG; and 5-methyl-cytosine-DNA glycysolase, etc. (Krokan et al., *Biochem J*. 325:1-16 (1997) and Sun et al., *J. Biol. Chem.* 270:19501-8 (1995)).

The phrase "uracil DNA glycosylase" (UDG/UNG) is used herein to refer to an enzyme that is capable of cleaving the glycosyl bond between the base uracil and the sugar deoxyribose, only when the monomeric nucleotide dUTP is incorporated into a DNA molecule, resulting in incorporation of a deoxyuridine moiety (Duncan, B. in *The Enzymes* 14:565 (1981), ed.: Boyer P.). The enzyme does not act upon free dUTP, free deoxyuridine, or RNA (Duncan, supra).

The phrase "thermostable glycosylase" is used herein to refer to a glycosylase enzyme that is relatively stable to heat and/or degradation and is capable of catalyzing the cleavage of the glycosyl bond from a molecule. For example, a glycosylase is considered thermostable when it retains at least 5%, or at least 10%, or at least 15%, or at least 20%, or at least 25%, or at least 30%, or at least 35%, or at least 40%, or at least 40%, or at least 45%, or at least 50%, or at least 55%, or at least 60%, or at least 65%, or at least 70%, or at least 75%, or at least 80%, or at least 85%, or at least 90%, or at least 95% of the original glycosylase activity after heating, for example, at 95° C. for 30 minutes.

The phrase "thermostable DNA glycosylase" is used herein to refer to any DNA glycosylase that is relatively stable to heat and/or degradation and is capable of cleaving the N-glycosyl bond between the target base and deoxyribose releasing a free base and leaving an apurinic/apyrimidinic site. For example, a DNA glycosylase is considered thermostable when it retains at least 5%, or at least 10%, or at least 15%, or at least 20%, or at least 25%, or at least 30%, or at least 35%, or at least 40%, or at least 40%, or at least 45%, or at least 50%, or at least 55%, or at least 60%, or at least 65%, or at least 70%, or at least 75%, or at least 80%, or at least 85%, or at least 90%, or at least 95% of the original DNA glycosylase activity after heating, for example, at 95° C. for 30 minutes.

The phrase "thermostable uracil DNA glycosylase (UDG)" as used herein, refers to an enzyme that is relatively stable to heat and/or degradation and is capable of catalyzing the cleavage of the glycosyl bond between the deoxyribose of the DNA sugar-phosphate backbone and the uracil base (see U.S. Pat. No. 5,035,996 and Sandigursky, et al., *J. Biol. Chem.* 275(25):19146-19149, 2000). Although any UDGs or glycosylases may be used in the practice of the present invention, in some embodiments thermostable uracil DNA glycosylases may be used. A uracil DNA glycosylase is considered thermostable when it retains at least 5%, or at least 10%, or at least 15%, or at least 20%, or at least 25%, or at least 30%, or at least 35%, or at least 40%, or at least 40%, or at least 45%, or at least 50%, or at least 55%, or at least 60%, or at least 65%, or at least 70%, or at least 75%, or at least 80%, or at least 85%, or at least 90%, or at least 95% of the original uracil DNA glycosylase activity after heating at 95° C. for 30 minutes.

The term "incorporating" is used herein to mean becoming part of a nucleic acid polymer.

The term "terminating" is used herein to mean causing a treatment to stop. The term includes both permanent and temporary or conditional stoppages. For example, if a treatment were enzymatic, a permanent stoppage might be heat denaturation of the molecule or molecules that catalyzes the enzymatic treatment. A conditional stoppage might be, for example, incubation at a temperature outside the active range of the molecule or molecules that catalyzes the enzymatic treatment but at which temperature the molecules are not made permanently inactive. Both types of termination are intended to fall within the scope of this term.

The term "oligonucleotide" is used herein to refer to varying lengths of single-stranded nucleic acid molecules (RNA or DNA). The term is used collectively and interchangeably with other terms of the art such as "polynucleotide" and "probe." Note that although oligonucleotide, polynucleotide, and probe are distinct terms of art, there is no exact dividing line between them. These terms are used interchangeably herein.

The term "primer" is used herein to refer to a single-stranded oligonucleotide or a single-stranded polynucleotide that is capable of being extended by covalent addition of nucleotide monomers, for example, during an amplification reaction. Nucleic acid amplification often is based on nucleic acid synthesis by a nucleic acid polymerase. Many such polymerases require the presence of a primer that can be extended to initiate such nucleic acid synthesis.

The phrase "oligonucleotide-dependent amplification" is used herein to refer to amplification using an oligonucleotide, or polynucleotide, or probe or primer to amplify a nucleic acid molecule. An oligonucleotide-dependent amplification is any amplification that requires the presence of one or more oligonucleotides or polynucleotides or probes or primers that are two or more mononucleotide subunits in length and end up as part of the newly formed, amplified nucleic acid molecule.

As used herein, the term "non-functional", when used in reference to a primer, means that the primer is substantially incapable of engaging in amplification reactions with respect to nucleic acid molecules with which the primer contains complementary sequences. In many instances, when a primer is rendered non-functional, it will be of insufficient length to hybridize to nucleic acid molecules to which it shares complementarity. As one skilled in the art would recognize, whether two nucleic acid molecules will hybridize to each other various with a number of factors, including the lengths of the nucleic acid molecules, the lengths of the regions of complementarity shared between the two nucleic acid molecules, and the conditions (e.g., temperature, salt concentrations, etc.) under which the two nucleic acid molecules are contacted with each other. Thus, in particular instances, whether a primer is non-functional will vary with the conditions under which it is contacted with nucleic acid molecules with which it shares sequence complementarity.

The phrase "thermostable polymerase" is used herein to refer to an enzyme that is relatively stable to heat and is capable of catalyzing the formation of DNA or RNA from an existing nucleic acid template. A polymerase is considered thermostable when it retains at least 5%, or at least 10%, or at least 15%, or at least 20%, or at least 25%, or at least 30%, or at least 35%, or at least 40%, or at least 40%, or at least 45%, or at least 50%, or at least 55%, or at least 60%, or at least 65%, or at least 70%, or at least 75%, or at least 80%, or at least 85%, or at least 90%, or at least 95% of the original polymerase activity after heating at 95° C. for 30 minutes.

One example of a thermostable polymerase is a thermostable DNA polymerase, which is relatively stable to heat and is capable of catalyzing the polymerization of nucleoside triphosphates to form primer extension products that are complementary to one of the nucleic acid strands of the target sequence. The enzyme initiates synthesis at the 3' end of the primer and proceeds in the direction toward the 5' end of the template until synthesis terminates.

The thermostable DNA polymerase most commonly used in PCR is Taq polymerase, isolated from the thermophilic bacterium *Thermus aquaticus* (Saiki, R. K. et al., *Science* 239:487-491 (1988); U.S. Pat. Nos. 4,889,818 and 4,965,188). Taq polymerase functions optimally at temperatures of 70-80° C., and is able to maintain substantial activity upon repeated exposure to temperatures of 92°-95° C. as are often used in the initial steps of PCR (Gelfand, D. H., & White, T. J., in *PCR Protocols: A Guide to Methods and Applications,*

Innis, M. A. et al., eds., Academic Press (1989), pp. 129-141; Bej, A. K., & Mahbubani, M. H., in *PCR Technology: Current Innovations*, Griffin, H. G., and Griffin, A. M., eds., CRC Press (1994), pp. 219-237).

The use of Taq polymerase in PCR eliminates the need to add fresh enzyme to the reaction mix prior to each PCR cycle. Instead, a quantity of Taq polymerase sufficient to catalyze DNA polymerization over the desired number of cycles can be mixed with the other components prior to the initiation of the first PCR cycle, and the enzyme continues to function throughout the repetitive cycles of increased and decreased temperatures. The use of Taq polymerase also facilitates the automation of the PCR process (Gelfand, D. H., & White, T. J., in *PCR Protocols: A Guide to Methods and Applications*, Innis, M. A., et al., eds., Academic Press (1989), pp. 129-141), thereby at once dramatically reducing time constraints and the risks of operator error and sample contamination that are problematic with thermo-labile polymerases. Currently, most PCR amplification of nucleic acids for industrial and academic applications is performed using Taq polymerase and automated thermal cycling instrumentation.

In addition to Taq polymerase, other thermostable polymerases have found similar application in PCR (Bej, A. K., & Mahbubani, M. H., in *PCR Technology: Current Innovations*, Griffin, H. G., & Griffin, A. M., eds., CRC Press (1994), pp. 219-237). Specifically, recombinant Taq polymerases (Platinum® Taq or ACCUPRIME Taq) are also useful. In addition, substitutes for Taq polymerase in PCR are polymerases isolated from the thermophilic bacteria *Thermus thermophilus* (Tth polymerase), *Thermococcus litoralis* (Tli or VENT™ polymerase), *Pyrococcus furiosus* (Pfu or DEEPVENT polymerase), *Pyrococcus woosii* (Pwo polymerase) and other Pyrococcus species, *Bacillus sterothermophilus* (Bst polymerase), *Sulfolobus acidocaldarius* (Sac polymerase), *Thermoplasma acidophilum* (Tac polymerase), *Thermus flavus* (Tfl/Tub polymerase), *Thermus ruber* (Tru polymerase), *Thermus brockianus* (DYNAZYME™ polymerase), *Thermotoga neapolitana* (Tne polymerase; See WO 96/10640), *Thermotoga maritima* (Tma polymerase; See U.S. Pat. No. 5,374,553) and other species of the Thermotoga genus (Tsp polymerase), *Methanobacterium thermoautotrophicum* (Mth polymerase), and mutants thereof. While each of these polymerases is useful for particular applications (see, Bej, A. K., & Mahbubani, M. H., in: *PCR Technology: Current Innovations*, Griffin, H. G., & Griffin, A. M., eds., CRC Press (1994), pp. 219-237, at p. 222), Taq polymerase is still by far the most commonly used polymerase in PCR.

It is to be understood, however, that thermostable enzymes from other organisms may also be used in the present invention without departing from the scope or alternative embodiments. As an alternative to isolation, thermostable enzymes are available commercially from, for example, Invitrogen Corporation (Carlsbad, Calif.), New England Biolabs (Beverly, Mass.), Finnzymes Oy (Espoo, Finland) and Perkin Elmer Cetus (Norwalk, Conn.).

The term "sample" is used herein to refer to any nucleic-acid-containing specimen to be tested. The sample can be any biological material that contains nucleic acid molecules suitable for practicing the methods of the invention. The term can refer to, for example, virtually any liquid, solid, colloidal, suspension, gels, etc. The sample can be derived from any desired source, such as a physiological fluid, for example, blood, serum, plasma, saliva, ocular lens fluid, cerebral spinal fluid, sweat, urine, milk, ascites fluid, mucous, synovial fluid, peritoneal fluid, amniotic fluid or the like. Samples can be pre-treated prior to use, such as preparing plasma from blood, diluting viscous liquids, etc. or can be directly used in the methods and compositions of the invention. Methods of pretreatment can also involve separation, filtration, distillation, concentration, inactivation of interfering components, and the addition of reagents. Besides physiological fluids, other liquid samples may be used such as water, food products, etc.

Once the sample is obtained, nucleic acid may be prepared by methods that are well-known in the art (see, for example, Sambrook, J., et al., *Molecular Cloning: A Laboratory Manual*, $2^{nd}$ ed., Cold Spring Harbor Laboratory Press, Cold Spring Harbor, N.Y. (1989), pp. 9.16-9.23; Kaufman, P. B., et al., *Handbook of Molecular and Cellular Methods in Biology and Medicine*, CRC Press, Boca Raton, Fla., pp. 1-26 (1995)). Nucleic acid may also be extracted by using ready-made kits and procedures commercially available, e.g., QIAamp spin column procedure (QIAGEN, CA). Alternatively, the sample containing nucleic acid molecules may be used directly in methods and compositions of the invention.

Conventional techniques and terminologies of molecular biology and nucleic acid chemistry, which are within the skill of the art that may be used in the methods and compositions of the invention are also fully explained in the literature. See, for example, Sambrook et al., Molecular Cloning—A Laboratory Manual, Cold Spring Harbor Laboratory, Cold Spring Harbor, N.Y. (1989); Oligonucleotide Synthesis (M. J. Gait, ed., 1984); and Methods in Enzymology (Academic Press, Inc.).

The term "purified" is used herein to indicate that a molecule of interest has been separated from some or all other surrounding molecules and/or materials. "Purified" is thus a relative term, which is based on a change of the desired molecule in close proximity to other molecules, i.e. in a free state. Enzymes, for example, which adhere to, attach to, bind to (covalently or non-covalently), and/or associate with other biological or non-biological material after cell lysis are considered to be purified when at least some cellular debris, proteins and/or carbohydrates are removed by washing. These same enzymes are purified again, when they are released from other materials using methods or compositions of the invention.

The term purified is not intended to mean that all of the matter intended to be removed is removed from the molecules being purified. Thus, some amount of contaminants may be present along with the purified molecules. For practical applications, the concentration of materials such as water, salts, and buffer are not considered when determining whether a biological molecule has been purified. As an example, any biological molecules that have been separated from other molecules using column chromatography, but have been diluted with an aqueous buffer in the process, are still considered purified resulting from the chromatographic separation process.

The term "isolated" is used herein to indicate that a molecule of interest has been separated from substantially all of the molecules and/or materials that it is associated with it in its natural state. Alternatively, isolated means when the molecule is set apart or free from other molecules. To determine whether a biological molecule has been isolated, the concentration of materials such as water, salts, and buffer are not considered when determining whether a biological molecule has been "isolated."

Overview

Figure 2:
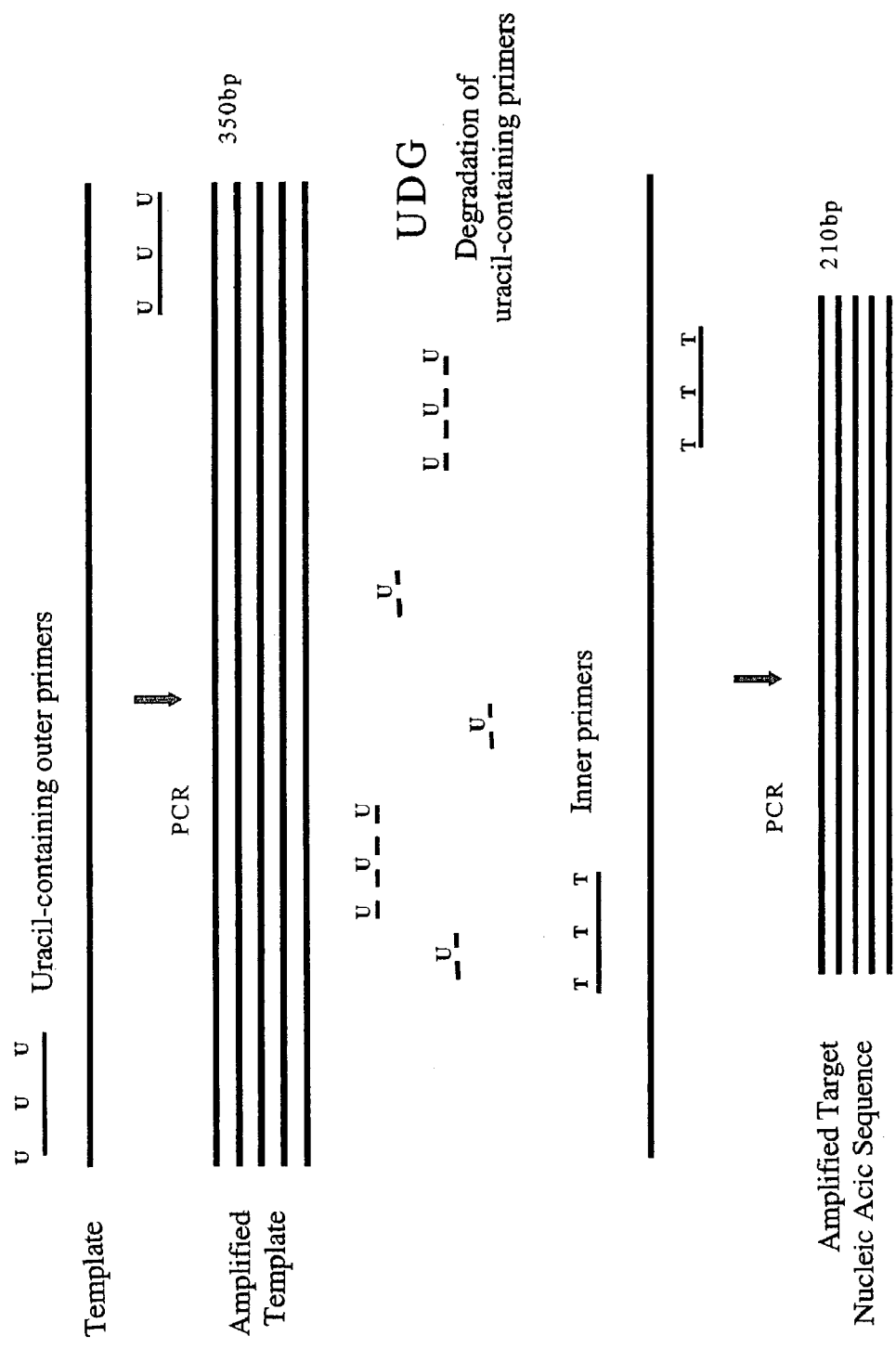
FIG. 2. Schematic drawing of an exemplary one tube nested PCR process of the invention.

With reference to FIG. 2, the present invention makes use of the combination of exo-sample nucleotide-containing outer primers, an agent that renders such primers substantially non-functional, and one or more inner primers to provide a simplified nested PCR reaction protocol. For example, one or more uracil-containing outer primers, UDG and one or more inner primers may be used to practice the methods of the present invention. As exemplified in FIG. 2, the exo-sample-nucleotide-containing outer primers (shown as U-containing oligonucleotides) are used to amplify a template nucleic acid molecule that comprises a target nucleic acid sequence to produce an amplified template molecule (shown as a 350 bp nucleic acid molecule). During the course of the amplification, the presence of UDG in the reaction mixture gradually reduces the concentration of uracil-containing outer primers that are capable of engaging in the amplification reaction. As the reaction proceeds, the concentration of inner primers (shown as T-containing oligonucleotides) increases relative to the concentration of outer primers. Further, the inner primers anneal to the amplified template molecules and are extended to produce amplified target nucleic acid sequence (shown as a 210 bp product in FIG. 2).

Methods of the invention permit the specific amplification (e.g., by nested PCR) of a target nucleic acid sequence from a template nucleic acid molecule in a single tube reaction. The present invention obviates the need to open the PCR tube between PCR reactions as required by the prior art, thereby eliminating a major source of potential contamination. The present invention may be used in conjunction with any nested PCR system known to those of skill in the art to generate an amplified target nucleic acid sequence without opening the PCR tube during the PCR reaction containing both outer and inner primers, thereby decreasing the chance of contamination. In one embodiment, for example, outer primers containing one or more uracils in place of one or more thymidines are used to conduct a nested PCR reaction.

In some embodiments of the present inventions, a reaction mixture containing both outer and one or more inner primers is used. One or more of the outer primers may contain one or more uracil and/or one or more other exo-sample nucleotides in place of one or more nucleotides making the primers susceptible to degradation by an appropriate agent, i.e., UDG digestion. At the beginning of the PCR reaction, the outer primers initiate the amplification of the template nucleic acid molecule. The amplified template serves as an additional template for the inner primers. By using one or more outer primers containing one or more exo-sample nucleotides (e.g., uracil) and the presence of an appropriate agent (e.g., UDG) in the system, the outer primers are slowly rendered non-functional thereby effectively removing them from the reaction mixture. The inner primers gradually become more utilized as the number of cycles increases and the effective concentration of the outer primers is decreased.

In one embodiment of the invention, different combinations of exo-nucleotide-containing primers and primers that do not contain exo-nucleotides are used in a one-tube reaction (e.g., one outer primer containing one or more exo-sample nucleotides may be used with one outer primer and/or one inner primer without exo-sample nucleotides; or one or more outer primer containing exo-sample nucleotides may be used with two inner primers without exo-sample nucleotides; etc.).

The invention also includes methods which start out with substantially the same initial concentrations of outer and inner primers, but result in a semi-nested reaction, because one or more of the exo-sample containing primers has been digested by glycosylases.

The present invention may also be used to perform multiple nested PCR reactions using multiple (3, 4, 5, 6, etc.) sets of primers or multiple semi-nested PCR reactions in combination with standard nested PCR reactions. For example, in a multiple semi-nested PCR reaction, an outer primer may contain one or more dUTP residues, one inner primer may contain one or more BdUR residues, and a third primer pair may contain no exo-sample nucleotide. Exposure of the primary reaction to UDG may then be used to degrade uracil containing products or primers without affecting BdUR containing products or primers. However, in subsequent reactions, exposure of the sample to light may be used to degrade BdUR containing primers and products, which then allows only the third primer pair to be utilized. Thus, conditions can be adjusted such that only one specific PCR product is generated in substantial quantities from the semi-nested reaction.

This method can also be used in combination with classical nested reactions and with different exo-sample nucleotide-containing primers such that the semi-nested reaction using one primer pair can be alternated between classical nested reactions using two primer pairs. For example, the primary reaction may be a nested reaction but the secondary reaction may be a semi-nested reaction. The third reaction may be a semi-nested reaction and the fourth reaction may be a nested reaction, etc. Other variations on this embodiment may be envisioned by those of ordinary skill in the art and are within the scope of the invention.

The invention further includes methods for performing nested amplification of target nucleic acid molecules in which exo-sample nucleotides are incorporated into amplification products. These exo-sample nucleotides may be incorporated in a number of ways. For example, exo-sample nucleotides may be incorporated by incorporation of a primer which contains one or more exo-sample nucleotides. Another way that exo-sample nucleotides may be incorporated into an amplification product is by carrying out the amplification reaction in the presence of one or more exo-sample nucleotide triphosphates.

The incorporation of exo-sample nucleotides into amplification products can be used, for example, to prepare nucleic acid molecules which can be rendered substantially unamplifiable at a later period in time (e.g., in later amplification processes). Thus, the incorporation of exo-sample nucleotides into amplification products can be used to prevent or reduce the amount of carry-over contamination of amplification products in later amplification reactions. Methods for using exo-sample nucleotides to reduce carry-over contamination are described, for example, in U.S. Pat. No. 5,945,313, the entire disclosure of which is incorporated herein by reference.

One method which may be used to reduce carry-over contamination in amplifications is to amplify nucleic acid molecules using one or more primers which contain one or more exo-sample nucleotides, in the presence of exo-sample nucleotide triphosphates. In particular instances, at least one of the exo-sample nucleotides present in the primers will be a different exo-sample nucleotide triphosphate present in the amplification reaction mixture. Thus, it will be possible to rendered the exo-sample nucleotide containing primers non-functional without affecting the amplification products being generated. Further, in cases where the amplification products pose a risk of carry-over contamination, compositions which contain these amplification products can be treated with an agent or incubated under conditions which render nucleic acid molecules which contain one or more particular exo-sample nucleotides substantially unamplifiable.

One specific example of the above is where nested amplification is conducted, according to methods described elsewhere herein, where both outer primers contain BdUR and deoxyuracil, both inner primers contain deoxyuracil, and amplification of a target nucleic acid molecules occurs in the presence of dUTP. In this instance, outer primers may be rendered non-functional by exposure to light during and/or between amplification reactions. Thus, the predominant end product of the amplification reactions is a nucleic acid product which is amplified by extension of the inner primers and contains deoxyuracil which is incorporated into the amplification product both from the primers and by nucleic acid synthesis. A nucleic acid molecule of this type may be rendered substantially unamplifiable by treatment with UDG, as described elsewhere herein. In related embodiments, exo-sample nucleotides used to prevent carry-over contamination may be omitted from one or both of the outer primers, one or both of the inner primers, or one or both sets of primers. Thus, in instances where nucleic acid molecules prepared as described above represent carry-over contamination in amplification reaction mixtures intended for the amplification of other nucleic acid molecules, nucleic acid molecules prepared as described may be rendered substantially unamplifiable.

The invention thus provides, in part, methods for producing nucleic acid molecules which contain exo-sample nucleotides using nested amplification reactions. The invention also provides methods for reducing carry-over contamination which involve rendering nucleic acid molecules prepared by nested amplification methods described herein substantially unamplifiable. The invention further includes compositions and reaction mixtures for performing these methods, as well as reaction mixtures and amplification reaction products prepared using methods of the invention.

The methods of the present invention may be practiced in combination with known methods of analyzing the products of an amplification reaction.

For example, real time detection methodologies may be employed in combination with the methods of the invention. Suitable detection methodologies include detection of product formation using DNA-binding dyes that discriminate between single and double stranded DNA, e.g., SYBR Green I. Other suitable methods include fluorescence energy transfer (FRET) based methods. An example of such a method is described in U.S. Pat. No. 5,348,853 and Wang et al., *Anal. Chem.* 67:1197-1203 (1995) and uses a primer with a FRET acceptor label and an oligonucleotide complementary to the primer with a FRET donor. Prior to amplification, the labeled oligonucleotides form a primer duplex in which energy transfer occurs freely.

Then, asymmetric PCR is carried out to its late-log phase before one of the target strands is significantly overproduced. When used in conjunction with the present invention, one or more inner primers may be labeled with one or more energy donors or acceptors and one or more oligonucleotides complementary to a primer may be labeled with one or more energy acceptors or donors.

A second method for detection of amplification product suitable for use in conjunction with the methods of the present invention is the 5' nuclease PCR assay (also referred to as the TAQMAN™ assay) (Holland et al., *Proc. Natl. Acad. Sci. USA* 88:7276-7280 (1991); Lee et al., *Nucleic Acids Res.* 21:3761-3766 (1993)). This assay detects the accumulation of a specific PCR product by hybridization and cleavage of a doubly labeled fluorogenic probe (the "TAQMAN" probe) during the amplification reaction. Cleavage of the probe generates an increase in the fluorescence intensity of the reporter dye. When used in conjunction with the methods of the present invention, the TAQMAN® probe may be designed with a sequence that includes all or a portion of the target nucleic acid sequence to be amplified.

Another method of detecting amplification products suitable for use in conjunction with the methods of the present invention is the MOLECULAR BEACONS method (Tyagi and Kramer (*Nature Biotech.* 14:303-309 (1996)).

This method relies on the use of energy transfer using hybridization probes that can form hairpin structures. On one end of the hybridization probe (either the 5' or 3' end) there is a donor fluorophore, and on the other end, an acceptor moiety. In the absence of product, the probe is in a hairpin configuration and fluorescence is quenched. In the presence of the correct PCR product, the probe is in an "open conformation," and fluorescence is detected. As a result, the amount of fluorescence will increase as the amount of PCR product increases, and thus may be used as a measure of the progress of the PCR. When used in conjunction with the methods of the present invention, the MOLECULAR BEACONS probe may be designed with a sequence that includes all or a portion of the target nucleic acid sequence to be amplified.

Another method of detecting amplification products suitable for use in conjunction with the methods of the present invention is the SUNRISE PRIMER method of Nazarenko et al. (*Nucleic Acids Research* 25:2516-2521 (1997); U.S. Pat. No. 5,866,336). One primer of a primer pair consists of a single stranded primer with a hairpin structure at its 5'-end. The hairpin stem is labeled with a donor/quencher pair. The signal is generated upon the unfolding and replication of the hairpin sequence by polymerase. When used in conjunction with the methods of the present invention, one or more of the inner primers may be a SUNRISE PRIMER.

In some embodiments of the present invention, the nested PCR reactions of the present invention are performed using a LightCycler™, Roche Diagnostics Corporation, Indianapolis, Ind. Any of the above-mentioned detection systems and any other detection system known to those skilled in the art may be used in combination with the LightCycler™ apparatus in practicing the methods of the present invention.

Primers which may be used in methods of the invention, as well as included in compositions and kits of the invention, include random primers. Random primers may be used, for example, to amplify either substantially all of the nucleic acid present or a subclass of nucleic acid molecules present. In many instances, such primers will be used as outer primers. Further, these random primers may be designed so that they contain at least one of the same or different exo-sample nucleotides. These primers may be of any suitable length (e.g., at least 5, at least 6, at least 7, at least 8, at least 9, at least 10, at least 12, at least 15, at least 20, at least 25, at least 30, at least 40, at least 50, at least 60, at least 70, at least 80, at least 100, etc. nucleotides or from about 5 to about 60 nucleotides, from about 10 to about 50 nucleotides, from about 5 to about 15 nucleotides, from about 5 to about 30 nucleotides, from about 15 to about 50 nucleotides, from about 20 to about 50 nucleotides, from about 30 to about 100 nucleotides, etc.).

One example of a method for producing a random primer with at least one exo-sample nucleotide is where the primers are synthesize by solid phase synthesis in which mixtures of nucleotides are used to place nucleotides at particular positions in the primer. For example, a "random" 15-mer may be generated in which mixtures of nucleotides (e.g., a mixture containing dATP, dTTP, dCTP, dGTP, dUTP, etc) are used for the addition of nucleotides 1-7 and 9-15 in the primer and dUTP is introduced into the primer at position 8. Further, additional random primers may be synthesized in batches in which dUTP is specifically incorporated in only one of positions 1-7 and 9-15 in each batch and random nucleotides are introduced into the primers at position 8. Once these batches of random primers, each of which contains dUTP incorporated at least one position, have been prepared, the random primers of all of the batches may then be mixed to form a composition wherein essential all of the primers contain at least one exo-sample nucleotide located in at least one position.

As one skilled in the art would recognize, any number of exo-sample nucleotides may be incorporated into random primers, as well as other primers, suitable for use in methods of the invention. Also, in many instances, random primers, as well as other primers, suitable for use in methods of the invention will contain exo-sample nucleotides which are preferably not located near one or both termini of the primers (e.g., within 1, 2, 3, 4, 5, 6, or 7 nucleotides of one both termini) although an exo-sample nucleotide may be incorporated as the 3'-most nucleotide. This is so because, in some instances, incubation of such primers with agents or under condition which act upon the exo-sample nucleotide (e.g., resulting in cleavage of the primer) will not result in the primer becoming non-functional. Thus, the positions of exo-sample nucleotides in random primers may be designed so that incubation of such primers with agents or under condition which act upon the exo-sample nucleotide will render the primers non-functional (e.g., will generate primer fragments which are sufficiently short that they will not efficiently hybridize to nucleic acid molecules with which they share sequence complementarity under the particular hybridization conditions). Thus, the invention includes random primer compositions in which essentially all of the individual random primers contain at least one exo-sample nucleotide, as well as methods for using such random primers in methods of the invention and compositions containing such random primers.

In many instances, random primers will be used as outer primers for amplifying essentially all or at least a substantial portion of the nucleic acid present in a sample or a subclass of the nucleic acid molecules present. For example, random primers may be used in conjunction with target nucleic acid molecule specific inner primers and a polyT primer. In such an instance, the random primers and polyT primers, one or both of which may contain one or more of the same or different exo-sample nucleotides, may be used as outer primers which preferentially amplify nucleic acid molecules with polyA regions (e.g., cDNAs). Further, the inner primers may be designed to amplify a specific nucleic acid molecule, or subportion thereof, present in the population. Thus, the invention includes nested amplification methods in which (1) essentially all or at least a substantial portion of the nucleic acid present in a sample or a subclass of the nucleic acid molecules present is amplified and (2) a specific nucleic acid molecule, or subportion thereof, in the population is also amplified. The invention further includes compositions used in such methods, kits for performing such methods, and nucleic acid molecules prepared by such methods.

As noted above, exo-sample nucleotides can be used, in conjunction with an agent or conditions where one or more primers which contain these exo-sample nucleotides are rendered non-functional for purposes of becoming involved in amplification reactions, to decrease, in a time course fashion, the concentration of primers (e.g., primers which contain exo-sample nucleotides) which are capable of functioning in amplification reactions. This time course inactivation of primers may occur relatively linearly or step-wise. For example, when PCR reactions are performed using a series of temperature shifts in which the duration of the various temperature incubations and the time between PCR reaction cycles is kept both low and relatively constant, the result will often be a relatively linear time course decrease in the concentration of primer(s) which contain the exo-sample nucleotide(s). Of course, one factor which will affect the linearity of the time course degradation of exo-sample nucleotide containing primers, is the effect that the various temperature shifts within each amplification cycle has on the primer degradation rate.

Step-wise reductions in the concentration of primers which contain exo-sample nucleotides can occur in any number of ways. For example, when a primer contains an exo-sample nucleotide which renders the subject to cleavage by light (e.g., BdUR), incubations in the presence of light between amplification cycles can be used to render particular amounts of the primer non-functional. As a specific example, a reaction mixture which contains two outer primers, each of which contains multiple BdUR nucleotides, and two inner primers which do not contain any exo-sample nucleotides undergoes five PCR reaction cycles. Between each PCR reaction cycle, the PCR reaction mixture is exposed to identical intensities of light which will induce the cleavage of primers containing BdUR. After the first cycle, the reaction mixture is exposed to the light for 20 seconds. After the second cycle, the reaction mixture is exposed to the light for 40 seconds. After the third cycle, the reaction mixture is exposed to the light for 80 seconds. After the fourth cycle, the reaction mixture is exposed to the light for 160 seconds. If the PCR reaction mixture is incubated under conditions in which the BdUR containing primers are cleaved only when exposed to the light between PCR reaction cycles (e.g., the reaction mixtures are shielded from light during the PCR reaction cycles), then cleavage of the BdUR containing primers should occur in a relatively step-wise fashion, with roughly logarithmic decreases in functional primer concentrations at each step. Any number of variations of the above are possible and are included within the scope of the invention.

Further, methods of the invention include those where the amount of primers which contain one or more exo-sample nucleotides is substantially decreased in later amplification reaction cycles of a series. In other words, methods of the invention include those where the concentration of primers which contain one or more exo-sample nucleotides is substantially decreased prior to termination of the amplification reaction cycles which yield the desired amplified nucleic acid. In certain instances, a substantial decrease in the number of primers which contain one or more exo-sample nucleotides in later amplification reaction cycles of a series will be desirable so that the majority of nucleic acid molecules in the final reaction mixture are amplification products generated by amplification employing particular primers (e.g., the inner primers).

The invention thus includes methods for amplifying nucleic acid molecules in which the concentration of one or more primers is reduced, e.g., the primers are rendered non-functional, in time course fashion between and/or during reaction cycles. Further, as explained above, these primers may be rendered non-functional, for example, in a relatively linear manner with respect to time or in a stepwise manner.

The rendering of primers non-function may occur under conditions in which a particular percentage of the primers which contain one or more exo-sample nucleotides are rendered non-functional during and/or between each amplification cycle. Thus, the invention includes methods in which during any one amplification cycle and/or between each reaction cycle the concentration of one or more primers which contain one or more exo-sample nucleotides is decreased by at least 2%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%. The invention further includes methods in which the decrease in the concentration of one or more primers which contain one or more exo-sample nucleotides during any one amplification cycle and/or between each reaction cycle falls within one of the following ranges about 1% to about 95%, about 5% to about 95%, about 10% to about 95%, about 20% to about 95%, about 25% to about 95%, about 30% to about 95%, about 40% to about 95%, about 50% to about 95%, about 60% to about 95%, about 70% to about 95%, about 80% to about 95%, about 90% to about 95%, about 1% to about 90%, about 1% to about 80%, about 1% to about 70%, about 1% to about 60%, about 1% to about 50%, about 1% to about 40%, about 1% to about 30%, about 1% to about 20%, about 1% to about 10%, about 1% to about 5%, about 10% to about 90%, about 10% to about 80%, about 10% to about 70%, about 10% to about 60%, about 10% to about 50%, about 10% to about 40%, about 10% to about 30%, about 10% to about 20%, about 10% to about 15%, about 15% to about 90%, about 15% to about 70%, about 15% to about 50%, about 15% to about 40%, about 15% to about 30%, about 15% to about 20%, about 20% to about 90%, about 20% to about 60%, about 20% to about 40%, about 20% to about 30%, about 25% to about 90%, about 25% to about 60%, about 25% to about 40%, about 25% to about 30%, about 30% to about 90%, about 30% to about 60%, about 30% to about 50%, or about 30% to about 40%.

There are various UDGs commercially available. For example, *E. coli* UDG is available from Invitrogen Corp. (Carlsbad, Calif.). *E. coli* UDG is fairly thermostable under normal PCR conditions. A thermo-labile UDG that is useful in conventional PCR contamination control is available from Roche Diagnostics (Mannheim, Germany). In addition, other UDGs may be isolated from various organisms using standard biochemical techniques. For example, the isolation of a thermostable UDG is described in Sanigursky, et al., *J. Biol. Chem.* 275:19146-19149, 2000.

Although any UDG may be used in the practice of the invention, in some instances it may be desirable to use a more thermostable UDG, as it will continue to remove the uracil bases from the polynucleotides in a reaction mixture through more cycles of the amplification reaction thereby giving a more complete degradation of uracil-containing polynucleotides.

When UDG is included in a PCR reaction mixture it may be present at a concentration of from about 0.001 units/50 µl to about 50 units/50 µl of reaction mixture, or from about 0.01 units/50l µl to about 25 units/50 µl of reaction mixture, or from about 0.1 units/50 µl to about 10 units/50 µl of reaction mixture, or from about 0.1 units/50 µl to about 5 units/50 µl of reaction mixture, or from about 0.2 units/50 µl to about 2 units/50 µl of reaction mixture, or from about 0.25 units/50 µl to about 1 unit/50 µl of reaction mixture.

At the beginning of the PCR reaction, the outer primers initiate amplification of the template nucleic acid molecule. The concentration of U-containing primers and UDG may be adjusted such that the amplification of the template with the U-containing primers is the predominate reaction occurring for a desired number of cycles, typically ranging from 5-500 cycles, or typically 10, 15, 20, 25, 30, 35, 40, 50 cycles, etc. The amplified template serves as an additional template for the inner primers. By gradual depletion of the outer primers throughout the reaction and subsequent utilization/incorporation of the nested inner primers, a clear nested product is generated.

Thus, one tube nested PCR employs the same principles as classical nested PCR. However, there is no clear delineation between amplification of the template nucleic acid molecule using the outer primers and amplification of the target nucleic acid sequence using the inner primers, but rather both amplification reactions may occur simultaneously in the same tube. By using outer primers containing exo-sample nucleotides and incorporating a DNA glycosylase into the system, for example, the outer primers are degraded over time (essentially diluted) out of the system, while the inner primers gradually become more utilized as the amplification reaction progresses. Thus, the effective concentration of the inner primers-relative to that of the outer primers-increases during the course of the amplification reaction. Concomitantly, the amplification of the target nucleic acid sequence using the inner primers increases relative to the amplification of the template nucleic acid molecule using the outer primers.

Methods of the present invention may be used to perform multiple nested reactions containing a plurality of sets of primers (e.g., 2, 3, 4, 5, 6, 7, 8, 9, 10, etc. sets) so that the inner primers subsequently amplify specific target nucleotide sequences of the templates previously amplified by the outer primer pairs. Primer sequences may be selected such that each template nucleic acid molecule to be amplified using an outer primer pair contains a single target nucleic acid sequence to be amplified with one or more inner primers. In some embodiments, more than one target nucleic acid sequence (e.g., 2, 3, 4, 5, 6, 7, 8, 9, 10, etc.) may be amplified from a given template. Thus, outer primers may be selected so as to amplify a template that contains multiple target nucleic acid sequences that may be amplified using the appropriate inner primers.

Methods of the invention include those in which multiple exo-sample nucleotides are present in different primers and more than one different exo-sample nucleotide is present in one or more primers. For example, in a triple nested reaction, an outer primer or both members of an outer primer pair may contain incorporated dUTP, the next inner primer or member of an inner primer pair may contain BdUR and the innermost primers may contain no exo-sample nucleotides. The outermost, uracil-containing primers can be degraded using UDG, but the BdUR-containing primers are not degraded using UDG. The BdUR containing primer can later be degraded upon exposure to light, for example. Embodiments of this type may be performed using any exo-sample nucleotide known to those skilled in the art and may be carried out using multiple (e.g., 2, 3, 4, 5, 6, 7, 8, 9, 10, etc.) nested reactions containing unlimited numbers of primers (e.g. semi-nested, single-nested, double nested, triple nested, quadruple nested, etc.).

In particular embodiments of the invention, the exo-sample nucleotide used to distinguish amplification products herein is provided as part of an oligonucleotide, primer or probe before amplification. The methods of these embodiments, as well as other embodiments, are particularly applicable to any in vitro procedures which utilize enzymes to amplify specific nucleic acid sequences including, but not limited to, PCR, reverse transcriptase PCR (RT-PCR), rapid cycle capillary PCR and the like.

As exemplified herein, in certain embodiments of the invention, the basic amplification protocol PCR is modified in three ways, for example: (1) amplification is performed using outer one or more primers containing exo-sample nucleotides (e.g., one or more outer primers contain one or more deoxyuracil residues substituted for deoxythymidine); (2) an agent capable of reaction with the exo-sample nucleotide so as to render primers containing the exo-sample nucleotide non-functional are added to the PCR reaction mixture; and (3) amplification proceeds with the agent acting on exo-sample-nucleotide containing primers thereby reducing the ability of the outer primers to be used in the amplification reaction. The action of the agent may occur continuously during the amplification reaction or may occur discontinuously, i.e., only during certain portions of the reaction. Suitable agents include, but are not limited to, DNA glycosylases such as UDG. This method can be used to perform any nucleotide amplification protocol requiring the use of primers.

In other particular embodiments, the methods and/or compositions of the invention may be used in rapid-cycle capillary PCR reactions. The use of glass capillaries in rapid-cycle capillary PCR can increase the speed of analysis since glass shows much greater temperature conductivity than plastic. Those skilled in the art will appreciate that the use of the present invention in conjunction with capillary PCR methods overcomes the sample handling difficulties normally associated with classical nested PCR in a capillary PCR format. The amplified product can then be identified, for example, either by hybridization with fluorochrome labeled probes or by the resulting product's melting temperature using fluorescent dyes which are temperature sensitive and fluoresce according to different temperatures. Thus, by measuring the fluorescence intensity after each cycle of the PCR, product generation is monitored in real-time (see Wittwer, et al., *BioTechniques* 22:176-181 (1997) and Berg, et al., *BioTechniques* 29:680-4 (2000)).

Variations of the embodiments described above, as well as other embodiments, may be used in conjunction with high-throughput systems that allow the use of multi-tube systems, multi-welled chambered systems, or any multi-chambered or multi-apparatus systems. Additional embodiments of the invention include those in which high throughput systems that use PCR amplification or primers are employed. Examples of such embodiments and systems may be envisioned by those of ordinary skill in the art and are within the scope of the invention.

In other particular embodiments of the invention, methods and/or compositions described herein may be used in conjunction with and/or may include RT-PCR. In embodiments of this type, a cDNA is first generated from mRNA by using a reverse transcriptase (e.g., a reverse transcriptase with substantially reduced RNase H activity; see U.S. Pat. Nos. 6,063,608 and 5,668,005). After generation of the cDNA, specific primer pairs are typically employed in a nested amplification reaction to amplify specific target sequences from the cDNA that was previously generated.

Reverse transcriptases from any source-native or recombinant-may be used in the practice of the present invention. Suitable reverse transcriptases include, but are not limited to, those from Moloney murine leukemia virus (M-MLV), human T-cell leukemia virus type I (HTLV-I), bovine leukemia virus (BLV), Avian Sarcoma Leukemia Viruses (ASLV) including Rous Sarcoma Virus (RSV) and Avian Myeloblastosis Virus (AMV), human immunodeficiency virus (HIV), cauliflower mosaic virus, Saccharomyces, Neurospora, Drosophila, primates, and rodents. See, for example, U.S. Pat. Nos. 4,663,290 and 6,063,60; Grandgenett, D. P. et al., *Proc. Nat. Acad. Sci. (USA)* 70:230-234 (1973), Gerard, G. R., *DNA* 5:271-279 (1986), Kotewicz, M. L. et al. *Gene* 35:249-258 (1985), Tanese, N. et al. *Proc. Natl. Acad. Sci. (USA)* 82:4944-4948 (1985), Roth, M. J. et al., *J. Biol. Chem.* 260:9326-9335 (1985), Michel, F. et al., *Nature* 316:641-643 (1985), Akins, R. A. et al., *Cell* 47:505-516 (1986) and *EMBO J.* 4:1267-75 (1985), and Fawcett, D. F., *Cell* 47:1007-1015 (1986); Shinnick, T. M. et al., *Nature* 293:543-548 (1981); Seiki, M. et al., *Proc. Natl. Acad. Sci. USA* 80:3618-3622 (1983); Rice N. R. et al., *Virology* 142:357-77 (1985); Schwartz et al., *Cell* 32:853-869 (1983); Larder, B. et al., *EMBO J.* 6:3133-3137 (1987); Farmerie, W. G. et al., *Science* 236:305-308 (1987); Barr, P. J. et al., *BioTechnology* 5:486-489 (1987)); Tanese, N. et al., *J. Virol.* 59:743-745 (1986); Hansen, J. et al., *J. Biol. Chem.* 262: 12393-12396 (1987); Sonigo, P. et al., *Cell* 45:375-85 (1986); Takatsuji et al., *Nature* 319:240-243 (1986); Toh et al., *Nature* 305:827-829 (1983)); Alexander et al., *J. Virol.* 61:534-542 (1987); and Yuki, S. et al., *Nucl. Acids Res.* 14:3017-3030 (1986).

As an alternative to UDG treatment alone, UDG and a treatment that cleaves the sugar-phosphate backbone (remaining after UDG treatment) may be used. Such treatments that cleave the sugar-phosphate backbone may include, but are not limited to, heat, endonuclease IV, alkaline hydrolysis, tripeptides such as Lys-Trp-Lys and Lys-Tyr-Lys (Pierre et al., *J. Biol. Chem.* 256:10217-10220 (1981)), AP endonucleases such as endonuclease V, endonuclease III, endonuclease VI, endonuclease VII, human endonuclease II, and the like (Linn, S. *Nucleases Involved in DNA Repair in Nucleases*, Cold Spring Harbor Laboratory, ed. Linn, S. and Roberts, R. (1985)).

In alternate embodiments within the scope of the invention, other exo-sample nucleotides suitable for performing the methods of the invention may also be used. In particular embodiments of the invention, for example, deoxy-oligo-nucleotides containing bromodeoxyuridine (BdUR) may be used as the primers of the invention. Primers containing BdUR may be degraded upon exposure to light. Other exo-sample nucleotides that may be used in the compositions and/or methods of the invention, include, but are not limited to, 7-methylguanine, 5,6-dihydro-5,6-dihydroxydeoxythymidine, 3-methyldeoxadenosine, inosine, 5-bromo-deoxycitidine, 5-methyl-deoxycitidine, 5-bromo-deoxyuridine, O-6-methyl-deoxyguanosine, 5-iodo-deoxyuridine, 8-oxy-deoxyguanine, ethanoadenine, 5,6-dihydrouracil, etc. (see U.S. Pat. No. 5,334,515 and Duncan, B. K., The Enzymes XIV: 565-586 (1981). Any exo-sample nucleotide that may be incorporated into DNA may be used in this invention. Other exo-sample nucleotides may be envisioned by those of ordinary skill in the art and are also within the scope of the invention.

In particular embodiments of the invention, primers are used wherein, at one or more positions, one or more (e.g., 1, 2, 3, 4) of the four deoxy-ribonucleotides (dATP, dTTP, dCTP and dGTP), in the primers are replaced with one or more exo-sample nucleotides (e.g., 1, 2, 3, 4, 5, 6, 7, 8, 9, 10, etc.) which may be the same or different. For examples, particular embodiments utilizing primers with considerable numbers of the same or different exo-sample nucleotides may be used over those with fewer exo-sample nucleotide-containing primers. Primers with exo-sample nucleotides located throughout the primer may also be used. Primers with exo-sample nucleotides evenly spaced apart or separated by 2-3, 3-4, 5-6, 7-8, 9-10, 11-12, 13-14, 15-16, 17-18, 2-5, 3-8, 6-10, 8-12, 10-14, 12-16, 14-18, 16-20, 18-25, etc. nucleotides may also be used.

Primers having exo-sample nucleotides at or near (within 5 nucleotides) from the 3'-terminus may also be used. Primers having exo-sample nucleotides at or near (within 5 nucleotides) from the 5'-terminus may also be used. Primers with one exo-sample, optionally in the middle of the primer, may also be used.

Depending upon the conditions (i.e., temperature, ionic strength) used to conduct the amplification reaction, primers may be at least about 10, at least about 15, at least about 20, at least about 25, at least about 30, at least about 40, or at least about 50 nucleotides in length.

The methods of the invention are not strictly dependent on primer length, as any primer length suitable for practicing the methods of the invention may be used. For specific applications (i.e., nested PCR, standard PCR, RT-PCR, semi-nested PCR, etc.) primer lengths can be at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, etc. nucleotides. The range of primer lengths can also be from at least about 2 nucleotides to about 1000 nucleotides, from about 5 nucleotides to about 1000 nucleotides, from about 10 nucleotides to about 1000 nucleotides, from about 15 nucleotides to about 1000 nucleotides, from about 20 nucleotides to about 1000 nucleotides, from about 25 nucleotides to about 1000 nucleotides, from about 30 nucleotides to about 1000 nucleotides, from about 35 nucleotides to about 1000 nucleotides, etc. Primer lengths can also be longer than 1000, 2000, 3000, 4000, 5000 nucleotides, etc. The upper range of primer lengths may not be limited to the ranges as exemplified herein as any primer lengths and ranges may be suitable to practice the methods of the invention.

In particular embodiments that depend on two oligonucleotide primer pairs, the present invention is capable of rendering one or more primers of the outer primer pair substantially non-functional as long as one primer of the outer primer pair contains at least one exo-sample nucleotide. Those of ordinary skill in the art can empirically determine which primers or probes are acceptable during routine optimization and testing without undue experimentation.

For example, routine assay optimization, aimed at testing primer suitability, can be done by (1) making an exo-sample nucleotide-containing oligonucleotide, (2) performing a first nucleic acid amplification of a target sequence using that oligonucleotide, (3) seeding various amounts of the resulting first product in a new, second amplification that does not contain target sequences, (4) performing the second amplification in the presence of a glycosylase which is specific for the exo-sample nucleotide used, and (5) assaying the resultant second product for presence of nucleic acid molecules generated from the first amplification. All of these steps are routinely done as experimental controls and as part of normal validation of the method. The only additional work required of one practicing this embodiment involves routine synthesis of any additional oligonucleotides that may be required. Generally, if an oligonucleotide is observed to be not suitable, then a substitute can be easily found and similarly tested.

In particular embodiments of the invention, the initial concentrations of outer primer pair or inner primer pair may be at any concentration suitable for performing methods of the invention. Examples of such concentrations include about 0.01 μM, about 0.05 μM, about 0.1 μM, about 0.2 μM, about 0.3 μM, about 0.4 μM, about 0.5 μM, about 0.8 μM, about 1.0 μM, about 1.5 μM, about 2.0 μM, about 3.0 μM, about 4.0 μM, about 5.0 μM, about 8.0 μM, about 10.0 μM, about 15.0 μM, about 20.0 μM, etc. Similarly, the initial ranges of concentrations of the outer primer pair and/or the inner primer pair vary within ranges suitable for performing methods of the invention. Examples of such ranges of concentrations include from about 0.01 μM to about 0.2 μM, from about 0.01 μM to about 0.5 μM, from about 0.01 μM to about 1.0 μM, from about 0.01 μM to about 2.0 μM, from about 0.01 μM to about 5.0 μM, from about 0.1 μM to about 0.2 μM, from about 0.1 μM to about 0.5 μM, from about 0.1 μM to about 1.0 μM, from about 0.1 μM to about 2.0 μM, from about 0.1 μM to about 5.0 μM, from about 0.2 μM to about 0.5 μM, from about 0.2 μM to about 1.0 μM, from about 0.2 μM to about 2.0 μM, from about 0.2 μM to about 5.0 μM, from about 0.5 μM to about 1.0 μM, from about 0.5 μM to about 2.0 μM, from about 0.5 μM to about 5.0 μM, from about 1.0 μM to about 2.0 μM, from about 1.0 μM to about 5.0 μM, from about 1.0 μM to about 10.0 μM, from about 1.0 μM to about 20.0 μM, etc.

In another variation on this embodiment, an excess amount of inner primers may be used over the amount of the outer primers. The use of different primer concentrations between the two primer pairs may help to increase the incorporation of the inner primers over the outer primers during the nested reaction. For example, in specific embodiments of the invention, the initial ratio of inner primers to outer primers can be about 1:1, about 1.1:1, about 1.2:1, about 1.3:1, about 1.4:1, about 1.5:1, about 1.6:1, about 1.8:1, about 2.0:1, about 2.2:1, about 2.4:1, about 2.5:1, about 2.7:1, about 2.9:1, about 3.0:1, about 3.2:1, about 3.5:1, about 3.7:1, about 4.0:1, about 4.2:1, about 4.5:1, about 5.0:1, about 5.5:1, about 6.0:1, about 6.5:1, about 7.0:1, about 7.5:1, about 8.0:1, about 8.5:1, about 9.0:1, about 9.5:1, about 10.0:1, about 15:1, about 20:1, about 25:1, etc. In addition, the initial ranges of the ratio of inner primers to outer primers can be from about 1.0 to about 10.0, from about 1.1 to about 10.0, from about 1.5 to about 10.0, from about 1.1 to about 5.0, from about 1.5 to about 5.0, from about 2.0 to about 5.0, from about 2.5 to about 5.0, from about 3.0 to about 5.0, from about 1.1 to about 4.0, from about 1.2 to about 4.0, from about 1.5 to about 4.0, from about 2.0 to about 4.0, from about 2.0 to about 3.0, etc.

In another variation on this embodiment, an excess amount of outer primers may be used over the amount of the inner primers. This may be the case when random primers are used, for example. The use of different primer concentrations between the two primer pairs may help to increase the incorporation of the inner primers over the outer primers during the nested reaction. For example, in specific embodiments of the invention, the initial ratio of outer primers to inner primers can be about 1:1, about 1.1:1, about 1.2:1, about 1.3:1, about 1.4:1, about 1.5:1, about 1.6:1, about 1.8:1, about 2.0:1, about 2.2:1, about 2.4:1, about 2.5:1, about 2.7:1, about 2.9:1, about 3.0:1, about 3.2:1, about 3.5:1, about 3.7:1, about 4.0:1, about 4.2:1, about 4.5:1, about 5.0:1, about 5.5:1, about 6.0:1, about 6.5:1, about 7.0:1, about 7.5:1, about 8.0:1, about 8.5:1, about 9.0:1, about 9.5:1, about 10.0:1, about 15:1, about 20:1, about 25:1, etc. In addition, the initial ranges of the ratio of outer primers to inner primers can be from about 1.0 to about 10.0, from about 1.1 to about 10.0, from about 1.5 to about 10.0, from about 1.1 to about 5.0, from about 1.5 to about 5.0, from about 2.0 to about 5.0, from about 2.5 to about 5.0, from about 3.0 to about 5.0, from about 1.1 to about 4.0, from about 1.2 to about 4.0, from about 1.5 to about 4.0, from about 2.0 to about 4.0, from about 2.0 to about 3.0, etc.

In addition, modifications in annealing temperatures for the respective primer pairs may be at any temperature suitable for performing the methods of the invention. For example, a higher annealing temperature may be used for the inner primer pair to prevent binding of any remaining outer primers to the template during the nested PCR reaction. Examples of such temperatures for annealing primers to the templates may range from about 30° C. to about 90° C., from about 35° C. to about 85° C., from about 40° C. to about 80° C., from about 45° C. to about 75° C., from about 45° C. to about 70° C., from about 45° C. to about 55° C., from about 45° C. to about 65° C., etc. In some embodiments, it may be desirable to design the outer primers to have a higher annealing temperature.

Alternatively, modifications in the denaturing temperatures at any temperature suitable for performing the methods of the invention may also used. For example, a higher denaturing temperature may be used to prevent non-specific primer binding as well. Examples of such temperatures for denaturing primers may range from about 90° C. to about 97° C., from about 91° C. to about 96° C., from about 92° C. to about 95° C., from about 93° C. to about 95° C., from about 94° C. to about 95° C., etc.

Any one of these modifications may be used singly or in different combinations. For example, a higher concentration of inner primers may be used in combination with a lower annealing and denaturing temperature during nested amplification reactions, and so forth. Other modifications may be envisioned by those of ordinary skill in the art and are within the scope of the invention.

Kits

Kits of the invention may contain any number of various components suitable for practicing methods of the invention. One example of such components is instructions to carry out methods of the invention. Example of such instructions include those which direct individuals using the kits to perform methods for conducting PCR (e.g., nested PCR) in which the relative concentrations of one or more primers decreases with respect to one or more other primers during amplification of one or more target nucleic acid molecules.

As one skilled in the art would recognize, the full text of these instructions need not be included with the kit. One example of a situation in which kits of the invention would not contain such full length instructions is where directions are provided which inform individuals using the kits where to obtain instructions for practicing methods of the invention. Thus, instructions for performing methods of the invention may be obtained from Internet web pages, separately sold or distributed manuals or other product literature, etc. The invention thus includes kits, which direct users to locations where they can find instructions that are not directly packaged and/or distributed with the kits. These instructions may be in any form including, but not limited to, electronic or printed forms.

Kits may also contain instructions for performing nested PCR in which the relative concentration of one or more primers decreases with respect to one or more other primers during amplification of a target nucleic acid. In particular embodiments of the invention, a kit may contain either alone or in a master-mix format one or more of the following components in various combinations or individually: one or more thermostable DNA polymerases (either standard Taq, or recombinant Taq such as Platinum® Taq or ACCUPRIME Taq), one or more antibodies to the polymerase or polymerase subunits, one or more single strand binding proteins, one or more glycosylases such as UDG, one or more buffers, one or more nucleotides (e.g., one or more deoxynucleotides and/or one or more exo-sample nucleotides), $MgCl_2$ or solutions containing $MgCl_2$, one or more nucleotide triphosphates (e.g., one or more deoxynucleoside triphosphates), one or more primers containing one or more exo-sample nucleotides, one or more templates, one or more containers, one or more container containing water, and so forth. Optionally, a kit may include one or more primers such that at least one or more of the outer primers contain one or more exo-sample nucleotide. Other components of a kit for performing the methods of the invention may be envisioned by those of ordinary skill in the relevant art and are within the scope of the embodiment.

One example of a primer containing one or more exo-sample nucleotides which can be used in methods of the invention, and may be included in kits of the invention is a primer designed for the amplification of a cDNA target nucleic acid molecule generated from mRNA. A primer of this type may be designed to hybridize, for example, to cDNA sequences generated by reverse transcription of the polyA tail of the mRNA. Thus, primers suitable for use in particular methods of the invention and suitable for inclusion in kits of the invention include primers which are capable of hybridizing to nucleic acid molecules containing polyA or polyT regions which are at least about five, at least about ten, at least about fifteen, at least about twenty, at least about thirty, at least about forty, etc. nucleotides in length. Examples of such primers are primers containing a polyA or polyT region which is at least about five, at least about ten, at least about fifteen, at least about twenty, at least about thirty, at least about forty, etc. nucleotides in length. One or more exo-sample nucleotides, which may be the same or different, will generally be located within the region of the primer which shares homology to the target nucleic acid molecule. In many instances, it will be desirable to use exo-sample which do not interfere with hybridization of the primer to the target nucleic acid molecule. When the primer contains a polyT region, one example of such an exo-sample nucleotide is dUTP. Thus, the invention includes kits which contain primers suitable for use in methods of the invention, as well as the primers themselves, methods for using these primers, compositions comprising such primers and products generated using such primers.

A kit of the invention may comprise, for example, carrier means, such as a box, carton, tube or the like, having in close confinement therein one or more container means, such as vials, tubes, ampoules, bottles and the like. For example, a first container may contain a stable composition comprising a mixture of reagents, concentrated or at working concentrations, which may comprise at least one thermostable DNA polymerase, at least one buffer salt, at least one deoxynucleoside triphosphate, at least one exo-sample nucleotide, at least one thermostable uracil DNA glycosylase (UDG), etc. The amplification kit encompassed by this aspect of the present invention may further comprise additional reagents and compounds necessary for carrying out standard nucleic amplification protocols (see U.S. Pat. Nos. 4,683,195 and 4,683,202, which are directed to methods of DNA amplification by PCR).

For example, a first container may contain an oligonucleotide. A second container may contain an exo-sample containing oligonucleotide. A third container may contain a DNA polymerase, optionally a thermostable DNA polymerase, such as Taq DNA polymerase, or recombinant Taq polymerases (Platinum® Taq or ACCUPRIME Taq, Tne DNA polymerase, Tma DNA polymerase) or mutants or derivatives thereof. A fourth container may contain a uracil DNA glycosylase, alternatively a thermostable uracil DNA glycosylase.

The invention also provides, in part, kits for performing nested PCR.

Examples of such kits are ones which allow the practice of PCR methods in which the relative concentration of one or more (e.g., one, two, three, four, five, six, etc.) primers decreases with respect to one or more (e.g., one, two, three, four, five, six, etc.) other primers during amplification of one or more (e.g., one, two, three, four, five, six, etc.) target nucleic acid molecules.

Throughout herein, "a" or "an" is intended to mean one or more.

It will be readily apparent to those of ordinary skill in the relevant arts that other suitable modifications and adaptations to the methods and applications described herein are obvious and can be made without departing from the scope of the invention or any embodiment thereof. Having now described the present invention in detail, the same will be more clearly understood by reference to the following examples, which are included herewith for purposes of illustration only and are not intended to be limiting of the invention.

EXAMPLES

Materials and Methods

Nested PCR Conditions

One tube nested PCR using UDG was performed on several template nucleic acid molecules. Target nucleic acid sequences, including Y and X chromosome specific sequences, GAPDH, MYC and SSBP genes, were amplified using the materials and methods of the invention. Comparisons have been made to conventional PCR using either primer set and to classical nested PCR. The one tube nested PCR system of the present invention out-performed individual primer sets in these comparisons, showing specificity and often an increased sensitivity. The materials and methods of the present invention may be used in conjunction with any known PCR system, for example, the capillary PCR/rapid cycler systems (e.g. Light-Cycler®) and real time PCR systems.

Template DNA was extracted from normal human male and female cells. Serial dilutions of target DNA were amplified using the various primers sets. The amount of template DNA included in each reaction ranged from 5 ng to 1 pg. PCR reactions were conducted using Platinum® Taq DNA polymerase from Invitrogen Corporation, Carlsbad, Calif. according to the suppliers instructions. UDG, when present, was used at a concentration of 0.5 units/50 µl reaction mixture.

The annealing temperatures of the primers were designed to be approximately 60° C. and primers sequences were selected using the Primer 3 program (http://www-genome.wi.mit.edu/cgi-bin/primer/primer3_www.cgi). The primer sequences and the annealing temperatures used are provided in Table 1 and the PCR cycles were programmed with the indicated annealing temperatures. The annealing temperature could either be the same or different for both sets of primers. Designing the primers to use the same annealing temperature showed no adverse effects to the amplification of the target nucleic acid sequence. The concentration of the outer primer pairs and inner primer pairs for each PCR reaction were as indicated in Table 1. Typically, the outer primer pair concentration was 0.2 µM and the inner primer pair concentration was 0.5 µM.

In some instances, the outer primers were designed to contain multiple uracils replacing normally occurring thymidine residues, evenly spaced (if possible) throughout the primer sequence, this was found to be adequate. Primers of this type may be designed such that uracil residues may be separated by from about 5 nucleotides to 20 nucleotides, or from about 5 nucleotides to about 15 nucleotides or from about 5 nucleotides to about 10 nucleotides. Spacing of uracils may be important when long primers, i.e., longer than about 20 nucleotides, are used. After excision of the uracil and cleavage of the phophodiester backbone of the primer, it is desirable to leave fragments that are sufficiently small so as not to hybridize under the annealing conditions used for the inner primers. Fragments below about 15 nucleotides in length are preferred. Thus, uracils may be spaced from about one every 15 nucleotides or less. Uracils may be located closer together than 5 nucleotides (i.e., may be adjacent, separated by 1 nucleotide, 2 nucleotides, etc.) if desired. In other instances, outer primers were also designed to contain only one uracil in the middle of the primer. Primers having uracils interspersed throughout the primer may also be used.

The cycle conditions generally followed the program below, but may be optimized for the individual primers sets:

94° C. - 2 minutes
94° C. - 1 minutes
X° C. - 1 minutes    } 20 cycles (primary reaction)
72° C. - 1 minutes
94° C. - 1 minutes
Y° C. - 1 minutes    } 25 cycles (secondary reaction)
72° C. - 1 minutes
72° C. - 5 minutes
4° C. - soak X and Y are the respective annealing temperatures of the outer and inner primers.

Alternatively, when the annealing temperatures of the outer and inner primers were the same, the cycling conditions were as follows:

94° C.-2 minutes
94° C.-1 minutes
X° C.-1 minutes    } 45 cycles (~ 20 primary + 25 secondary)
72° C.-1 minutes
72° C.-5 minutes
4° C.-soak X indicates the annealing temperature of the primers.

Example 1

Comparison of Nested PCR to PCR with Y-Chromosome Specific Primers Pairs Used Individually.

Figure 3:
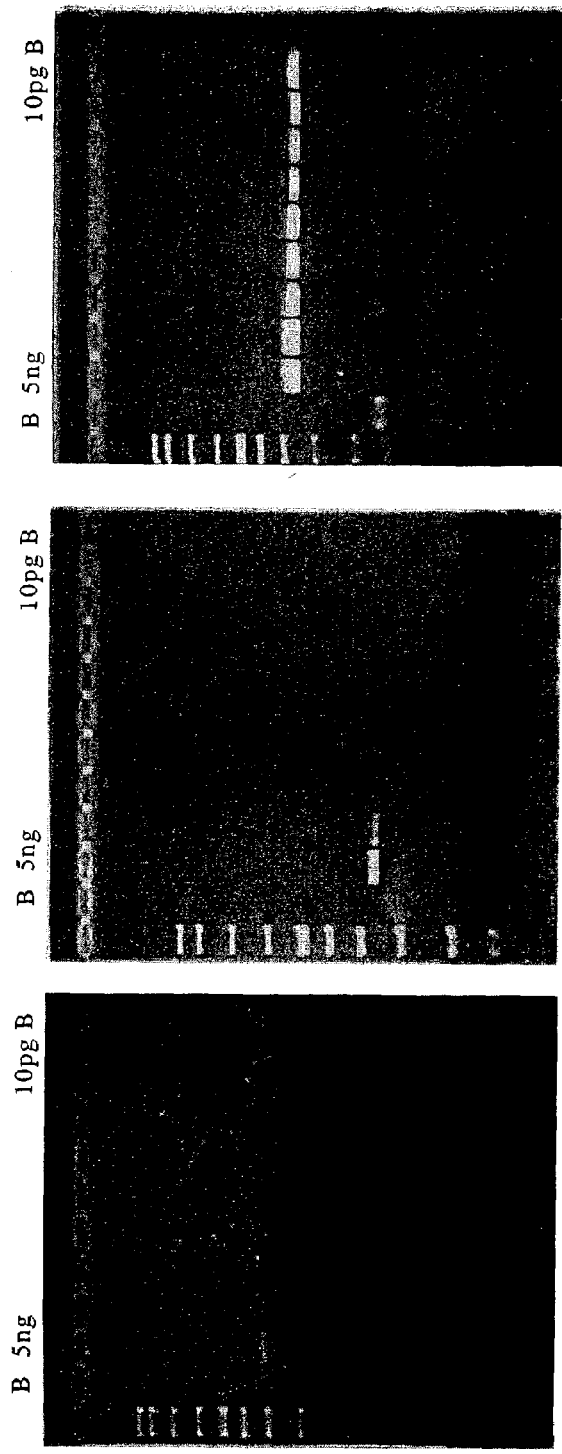
FIG. 3. Photographs of gels showing a comparison of nested PCR to standard PCR with Y-chromosome-specific primers pairs used individually.

With reference to FIG. 3, PCR reactions using individual Y-chromosome specific outer primer pair SEQ ID NO:1 and SEQ ID NO:2 (left panel) or inner primer pair SEQ ID NO:3 and SEQ ID NO:4 (center panel) are compared to nested PCR using both primer pairs together (right panel). The results illustrate the superiority of one tube nested PCR of the present invention over that of the primers used individually.

Each reaction contained varying amounts of template DNA and the results are shown in FIG. 3 where lane M contains a molecular weight ladder, lane 1 shows the results obtained with 5 ng of template DNA, lane 2 shows the results obtained with 1 ng of template DNA, lane 3 shows the results obtained with 0.5 ng of template DNA, lane 4 shows the results obtained with 0.25 ng of template DNA, lane 5 shows the results obtained with 0.1 ng of template DNA, lane 6 shows the results obtained with 75 pg of template DNA, lane 7 shows the results obtained with 50 pg of template DNA, lane 8 shows the results obtained with 25 pg of template DNA, and lane 9 shows the results obtained with 10 pg of template DNA. Lanes labeled with "B" denote the reagent blank controls.

The leftmost panel shows the results obtained with the outer primers alone, the center panel shows the results obtained with the inner primers alone and the right-most panel shows the results obtained by nested PCR using both primer pairs simultaneously. In the nested reaction, a product band is visible in the lane corresponding to the lowest amount of input template DNA. In contrast, neither primer pair alone produces a visible product band under these conditions.

Example 2

Comparison of Nested PCR to PCR with X-Chromosome Specific Primers Pairs Used Individually.

Figure 4:
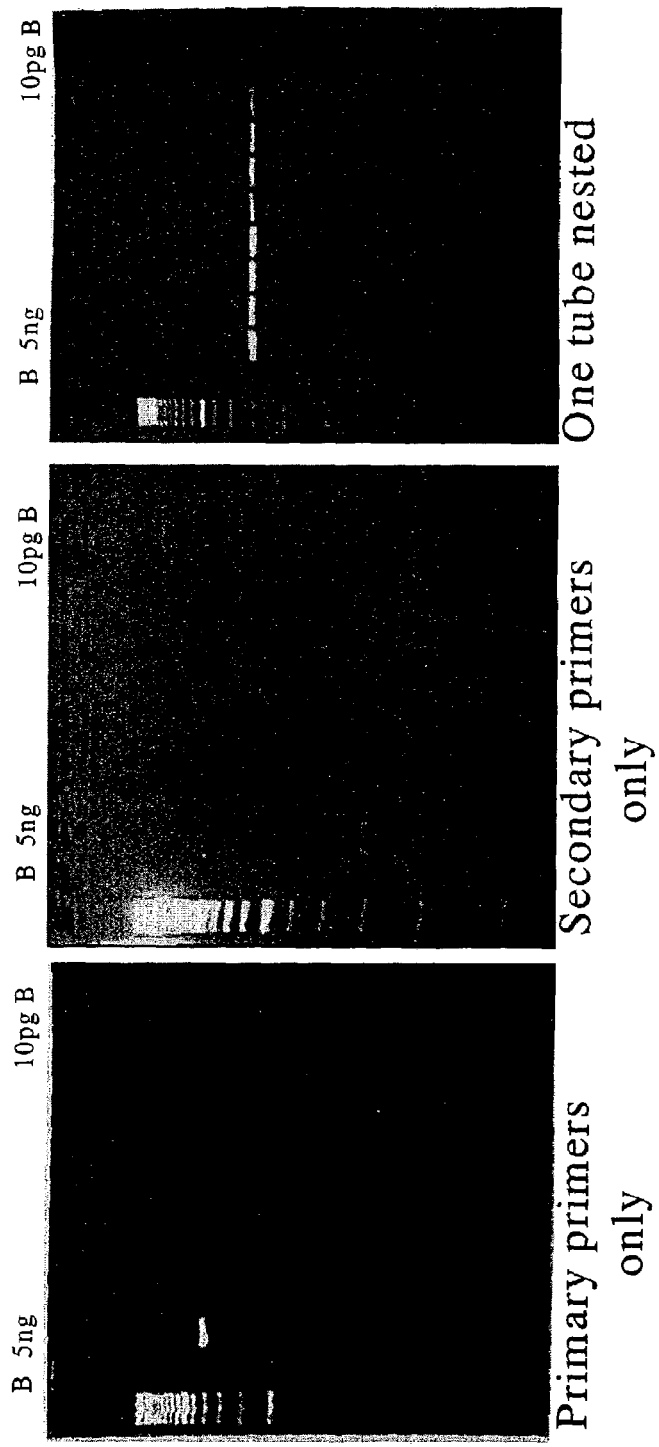
FIG. 4. Photographs of gels showing a comparison of nested PCR to standard PCR with X-chromosome-specific primers pairs used individually.

With reference to FIG. 4, PCR reactions using individual X-chromosome specific outer primer pair SEQ ID NO:9 and SEQ ID NO: 0 (left panel) or inner primer pair SEQ ID NO:11 and SEQ ID NO:12 (center panel) are compared to nested PCR using both primer pairs together (right panel). The results illustrate the superiority of one tube nested PCR of the present invention over that of the primers used individually.

Each reaction contained varying amounts of DNA and the results are shown in FIG. 4 where, for each reaction, lane M contains a molecular weight ladder, lane 1 shows the results obtained with 5 ng of template DNA, lane 2 shows the results obtained with 1 ng of template DNA, lane 3 shows the results obtained with 0.5 ng of template DNA, lane 4 the shows results obtained with 0.25 ng of template DNA, lane 5 shows the results obtained with 0.1 ng of template DNA, lane 6 shows the results obtained with 75 pg of template DNA, lane 7 shows the results obtained with 50 pg of template DNA, lane 8 shows the results obtained with 25 pg of template DNA, and lane 9 shows the results obtained with 10 pg of template DNA. Lanes labeled with "B" denote the reagent blank controls.

The leftmost panel shows the results obtained with the outer primers alone, the center panel shows the results obtained with the inner primers alone and the right-most panel shows the results obtained by nested PCR using both primer pairs simultaneously. In the nested reaction, a product band is visible in the lane corresponding to the lowest amount of input template DNA. In contrast, neither primer pair alone produces a visible product band under these conditions.

Example 3

Comparison of Classical Nested PCR to One Tube Nested PCR Using X-Chromosome Specific Primers.

Figure 5:
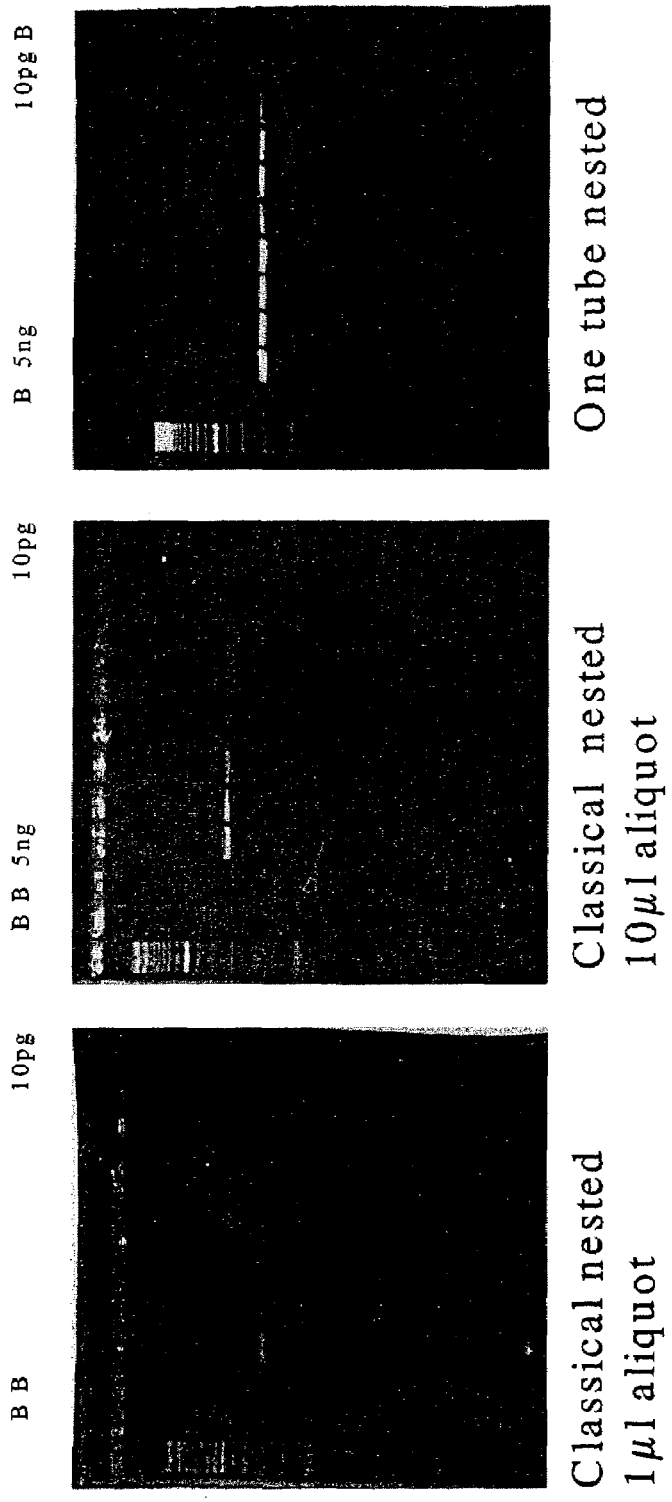
FIG. 5. Photographs of gels showing a comparison of classical nested PCR to one tube nested PCR using X-chromosome specific primers.

With reference to FIG. 5, classical nested PCR is compared to the one tube nested PCR of the present invention using X-chromosome specific primers. The results illustrate the superiority of one tube nested PCR of the present invention over that of classical nested PCR.

X-chromosome specific outer primer pair SEQ ID NO:9 and SEQ ID NO:10 and inner primer pair SEQ ID NO:11 and SEQ ID NO:12 were used for both classical and one tube nested PCR reactions. The outer primer pair reaction of the classical PCR reaction contained varying amounts of template DNA. After amplification with the outer primers, either a 1 µl (left panel) or a 10 µl (center panel) aliquot of the outer primer PCR reaction was used in the amplification reaction using the inner primers in the classical nested PCR reactions. The one tube nested PCR reaction contained varying amounts of template DNA as well as 0.5 units UDG/50 µl reaction mixture. Primer concentrations were as indicated in Table 1.

The results of the comparison of classical nested PCR and one tube nested PCR are shown in FIG. 5 where, for all reaction conditions, lane M contains a molecular weight ladder, lane 1 shows the results obtained with 5 ng of template DNA, lane 2 shows the results obtained with 1 ng of template DNA, lane 3 shows the results obtained with 0.5 ng of template DNA, lane 4 shows the results obtained with 0.25 ng of template DNA, lane 5 shows the results obtained with 0.1 ng of template DNA, lane 6 shows the results obtained with 75 pg of template DNA, lane 7 shows the results obtained with 50 pg of template DNA, lane 8 shows the results obtained with 25 pg of template DNA, and lane 9 shows the results obtained with 10 pg of template DNA. Lanes labeled with "B" denote the reagent blank controls.

In the nested reaction, a product band is visible in the lane corresponding to the lowest amount of input template DNA. In contrast, even when a 10 µl aliquot of the outer primer reaction is used, classical nested PCR does not produce a visible product band under these conditions.

Example 4

Effect of UDG on One Tube Nested PCR.

Figure 6:
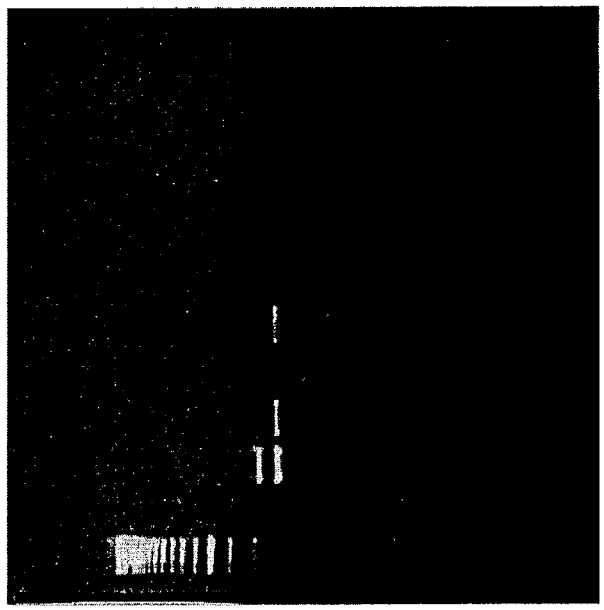
FIG. 6. Photograph of a gel showing the results obtained in a one tube nested PCR reaction in the absence of UDG.

X-chromosome specific outer primer pair SEQ ID NO:9 and SEQ ID NO:10 and inner primer pair SEQ ID NO:11 and SEQ ID NO:12 were used in a one tube nested PCR reaction as above except that UDG was omitted from the reaction mixture. FIG. 6 shows the results of one tube nested PCR reactions without the use of UDG. The results illustrate that when uracil-containing primers are used, UDG is required to eliminate unwanted product bands and to generate a clear product.

Lane M contains a molecular weight ladder, lane 1 shows the results obtained with 5 ng of template DNA, lane 2 shows the results obtained with 1 ng of template DNA, lane 3 shows the results obtained with 0.5 ng of template DNA, lane 4 shows the results obtained with 0.25 ng of template DNA, lane 5 shows the results obtained with 0.1 ng of template DNA, lane 6 shows the results obtained with 75 pg of template DNA, lane 7 shows the results obtained with 50 pg of template DNA, lane 8 shows the results obtained with 25 pg of template DNA, and lane 9 shows the results obtained with 10 pg of template DNA. Lanes labeled with "B" denote the reagent blank controls.

Example 5

One Tube Nested PCR Using GAPDH Primers.

Figure 7:
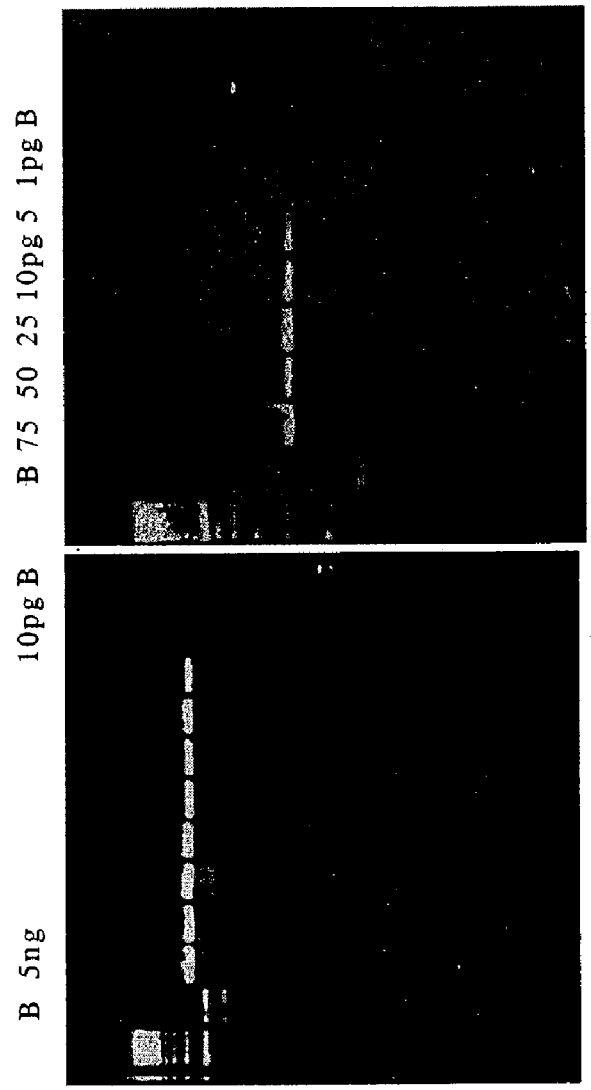
FIG. 7. Photographs of gels showing the results of a one tube nested PCR reaction using GAPDH primers.

With reference to FIG. 7, the results illustrate the superiority and clarity of one tube nested PCR reactions using GAPDH specific primers. GAPDH specific outer primer pair SEQ ID NO:17 and SEQ ID NO:18 and inner primer pair SEQ ID NO:19 and SEQ ID NO:20 were used in one tube nested PCR reactions using varying amounts of template DNA.

FIG. 7, left panel, shows the results obtained using DNA template amounts from 5 ng to 10 pg and the right panel shows the results obtained in a different experiment using DNA template amounts from 75 pg to 1 pg. In the left panel, lane M contains a molecular weight ladder, lane 1 shows the results obtained with 5 ng of template DNA, lane 2 shows the results obtained with 1 ng of template DNA, lane 3 shows the results obtained with 0.5 ng of template DNA, lane 4 shows the results obtained with 0.25 ng of template DNA, lane 5 shows the results obtained with 0.1 ng of template DNA, lane 6 shows the results obtained with 75 pg of template DNA, lane 7 shows the results obtained with 50 pg of template DNA, lane 8 shows the results obtained with 25 pg of template DNA, and lane 9 shows the results obtained with 10 pg of template DNA. Lanes labeled with "B" denote the reagent blank controls.

In the right panel, Lane M contains a molecular weight ladder, lane 1 shows the results obtained with 75 pg of template DNA, lane 2 shows the results obtained with 50 pg of template DNA, lane 3 shows the results obtained with 25 pg of template DNA, lane 4 shows the results obtained with 10 pg of template DNA, lane 5 shows the results obtained with 5 pg of template DNA, and lane 6 shows the results obtained with 1 pg of template DNA. Lanes labeled with "B" denote the reagent blank controls.

In the nested reaction, a product band is visible in the lane corresponding to 5 pg of input template DNA showing the sensitivity of the methods of the present invention.

Example 6

Detection of Diluted Y-Chromosome DNA (Y DNA) in X-Chromosome DNA (X DNA) Using Y-Chromosome Specific (Y-Specific) Primers in One Tube Nested PCR.

Figure 8:
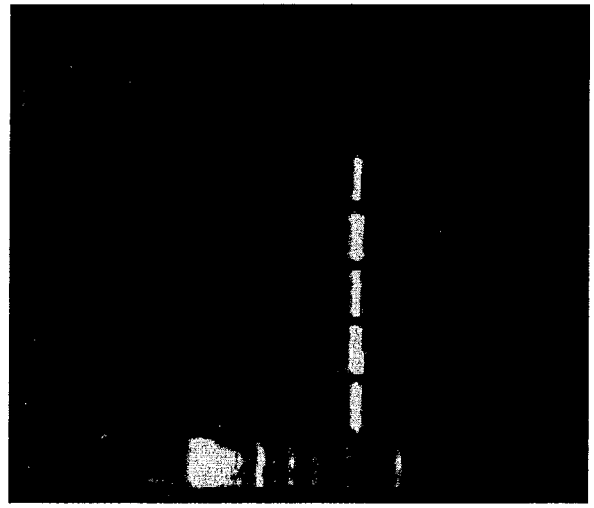
FIG. 8. Photograph of a gel showing the detection of diluted Y-chromosome DNA (Y DNA) in X-chromosome DNA (X DNA) using Y-chromosome specific (Y-specific) primers in one tube nested PCR.

With reference to FIG. 8, Y-chromosome containing DNA (male) was diluted into a background of X-chromosome containing DNA (female). Detection of the diluted Y DNA was carried out using Y-chromosome specific outer primer pair SEQ ID NO: 1 and SEQ ID NO:2 and inner primer pair SEQ ID NO:3 and SEQ ID NO:4. The results illustrate the ability of the one tube nested PCR system of the present invention to detect specific target DNA sequences in a background of non-desired sequences, i.e. to detect rare sequences.

The lanes are marked as follows: lane M contains a molecular weight ladder, lane 1 shows the results obtained when 0.5 ng Y DNA was used with no diluting X DNA, lane 2 shows the results obtained when 0.1 ng Y DNA was diluted with 4.9 ng X DNA, lane 3 shows the results obtained when 50 pg Y DNA was diluted with 4.950 ng X DNA, lane 4 shows the results obtained when 10 pg Y DNA was diluted with 4.990 ng X DNA, and lane 5 shows the results obtained when 2.5 pg Y DNA was diluted with 4.9975 ng X DNA. "X" denotes the presence of 0.5 ng of X DNA only. "B" denotes the reagent blank control.

Even with only 2.5 pg of Y-chromosome template DNA a clear signal is visible when contaminating DNA (X-chromosome) is present in a 2,000-fold excess (5 ng to 2.5 pg). This demonstrates the ability of the methods and materials of the present invention to detect rare target sequences.

All genes tested so far in the one tube nested PCR system, have shown sensitivity down to 10 pg DNA and some as low as 2.5 pg DNA (FIG. 8).

Clear, concise, single, nested product bands were produced, with no interference from other potential products (FIGS. 3-8). The one tube nested PCR showed superiority over the standard PCR carried out using the individual primers (FIG. 3 and FIG. 4). The one tube nested PCR also showed an increase in sensitivity over and above classical nested PCR (FIG. 5 and Table 1). Studies to exemplify the effect that UDG had on the nested PCR system showed the expected degradation of the outer primers, but also supported the requirement of these primers, and their subsequent depletion, to generate the single nested product band. The presence of uracil instead of thymidine in the outer primers showed no effect on their intrinsic priming ability.

In summary, the use of primers containing exo-sample nucleotides-for example, uracil containing primers-and an agent to degrade the exo-sample nucleotide-for example, UDG-in a one tube nested PCR system has proven to be very effective. Not only does it alleviate the major contamination issue associated with classical nested PCR, but also it is also more convenient and economical than classical nested PCR. It simplifies the process into a one-tube system and cuts down on reagents and time normally required for classical nested PCR. Nested PCR, as a rule, is more sensitive and specific than conventional PCR, and with this one tube innovation, it can be used easily, conveniently and with confidence.

Although the foregoing refers to particular embodiments, it will be understood that the present invention is not so limited. It will occur to those of ordinary skill in the art that various modifications may be made to the disclosed embodiments and that such modifications are intended to be within the scope of the present invention. All patents, patent applications and publications cited herein are fully incorporated by reference.

TABLE 1

| Primer pair | Target Gene Primer sequence | Annealing Temperature used | Lower limit of detection of initial target DNA using Outer and Inner primers alone | | One tube nested Primer Concentration | Lower limit of detection of initial target DNA | | | One tube nested PCR |
|---|---|---|---|---|---|---|---|---|---|
| | | | Outer | Inner | | Classical nested PCR Aliquots from primary PCR | | | |
| | | | | | | 1 μl | 10 μl | | |
| | SRY (Y Chromosome) | | | | | | | | |
| Outer | SRYFU-2 (SEQ ID NO:1) 5' uccuuugcacugaaagcug 3' | 58° C. | 0 | 0.01 ng | 0.2 μM | 5 ng | 0.5 ng | 0.0025 ng | |
| Outer | SRYRU-2 (SEQ ID NO:2) 5' agcggugcuccauucuuga 3' | 58° C. | | | 0.2 μM | | | | |
| Inner | SRYNF-2 (SEQ ID NO:3) 5' gagaatcccagaatgcgaaa 3' | 58° C. | | | 0.5 μM | | | | |
| Inner | SRYNR-2 (SEQ ID NO:4) 5' caattcttcggcagcatctt 3' | 58° C. | | | 0.5 μM | | | | |
| Outer | SRYFU-(SEQ ID NO:5) 5' aaggcaacguccaggauaa 3' | 58° C. | 5 ng | 0.5 ng | 0.2 μM | ND | ND | 0.01 ng | |
| Outer | SRYRU-(SEQ ID NO:6) 5' ucgcugcagaguaccgaag 3' | 58° C. | | | 0.2 μM | | | | |
| Inner | SRYNF-(SEQ ID NO:7) 5' catgaacgcattcatcgtgttc 3' | 67° C. | | | 0.5 μM | | | | |
| Inner | SRYNR-(SEQ ID NO:8) 5' ctgcgggaagcaaactgcaattctt 3' | 67° C. | | | 0.5 μM | | | | |
| | ATL (X Chromosome) | | | | | | | | |
| Outer | ATLFU-(SEQ ID NO:9) 5' gccuccuaagacugcugugg 3' | 58° C. | 1 ng | 0.025 ng | 0.2 μM | 0.05 ng | 0.025 ng | 0.01 ng | |
| Outer | ATLRU-(SEQ ID NO:10) 5' ucuuuggcccaguugcuagt 3' | 58° C. | | | 0.2 μM | | | | |
| Inner | ATL1F-(SEQ ID NO:11) 5' gaattaccacataggttgcact 3' | 62° C. | | | 0.5 μM | | | | |
| Inner | ATL1R-(SEQ ID NO:12) 5' ccctgatgaagaacttgtatctc 3' | 62° C. | | | 0.5 μM | | | | |

TABLE 1-continued

| Primer pair | Target Gene Primer sequence | Annealing Temperature used | Lower limit of detection of initial target DNA using Outer and Inner primers alone | | One tube nested Primer Concentration | Lower limit of detection of initial target DNA | | |
|---|---|---|---|---|---|---|---|---|
| | | | | | | Classical nested PCR Aliquots from primary PCR | | One tube nested PCR |
| | | 1TN/Class | Outer | Inner | | 1 μl | 10 μl | |
| | MYC | | 0.01 ng | 0.05 ng (−) | | 5 ng | 0.05 ng | 0.025 ng |
| Outer | MYCOFU (SEQ ID NO:13) 5' gccauuaccgguucuccaua 3' | 52° C./60° C. | | | 0.2 μM | | | |
| Outer | MYCORU (SEQ ID NO:14) 5' ccaaucgcuaugcuggauuu 3' | 52° C./60° C. | | | 0.2 μM | | | |
| Inner | MYCIF1 (SEQ ID NO:15) 5' tctttcttcggaccttctgc 3' | 52° C./60° C. | | | 0.5 μM | | | |
| Inner | MYCIR1 (SEQ ID NO:16) 5' cgttcaggtttgcgaaagta 3' | 52° C./60° C. | | | 0.5 μM | | | |
| | GAPDH | | 0.01 ng | 0.01 ng | | 0.01 ng | 0.01 ng | 0.005 ng |
| Outer | GAPDHFU (SEQ ID NO:17) 5' caggugacaguucgugaugc 3' | 58° C. | | | 0.2 μM | | | |
| Outer | GAPDHFR (SEQ ID NO:18) 5' cccacuggaaggcuuaccuc 3' | 58° C. | | | 0.2 μM | | | |
| Inner | GAPDHNF (SEQ ID NO:19) 5' ggtatggatgaggagctga 3' | 58° C. | | | 0.5 μM | | | |
| Inner | GAPDHNR (SEQ ID NO:20) 5' cttccacacagccctcgactaa 3' | 58° C. | | | 0.5 μM | | | |
| | B Actin | | 0.05 ng (−) | 0.01 ng | | 0.5 ng | 0.05 ng | 0.01 ng |
| Outer | B-ACTFU (SEQ ID NO:21) 5' actgcaucgtgauggactc 3' | 60° C. | | | 0.2 μM | | | |
| Outer | B-ACTRU (SEQ ID NO:22) 5' taacccucatgucaggcaga 3' | 60° C. | | | 0.2 μM | | | |

TABLE 1-continued

| Primer pair | Target Gene Primer sequence | Annealing Temperature used | Lower limit of detection of initial target DNA using Outer and Inner primers alone | | One tube nested Primer Concentration | Lower limit of detection of initial target DNA | | |
|---|---|---|---|---|---|---|---|---|
| | | | Outer | Inner | | Classical nested PCR Aliquots from primary PCR | | One tube nested PCR |
| | | | | | | 1 µl | 10 µl | |
| Inner | B-ACTF (SEQ ID NO:23) 5' acccacactgtgcccatct 3' | 60° C. | | | 0.5 µM | | | |
| Inner | B-ACTR (SEQ ID NO:24) 5' ggaaccgctccattgccaat 3' | 60° C. | | | 0.5 µM | | | |
| | HPRT | | | 0.01 ng(−) | | | — | 0.01 ng |
| Outer | HPRTFU-(SEQ ID NO:25) 5' attgtutgcagcaucaauaacatt 3' | 58° C. | 0 | | 0.2 µM | | | |
| Outer | HPRTRU-(SEQ ID NO:26) 5' ctggaautacatgtugccact 3' | 58° C. | | | 0.2 µM | | | |
| Inner | HPRTNF-(SEQ ID NO:27) 5' ttgaccaatttgaaacagtgagtt 3' | 58° C. | | | 0.5 µM | | | |
| Inner | HPRTNR-(SEQ ID NO:28) 5' acccagccgtatgttttctaataa 3' | 58° C. | | | 0.5 µM | | | |
| | G6PD | | 0 | 0.025 ng | | 5 ng | 0.5 ng | 0.025 ng |
| Outer | G6PDFU-(SEQ ID NO:29) 5' acgtgaugcagaaccaccua 3' | 57° C. | | | 0.2 µM | | | |
| Outer | G6PDRU-(SEQ ID NO:30) 5' gccttcccuggtcacauagt 3' | 57° C. | | | 0.2 µM | | | |
| Inner | G6PDNF-(SEQ ID NO:31) 5' ctgcagatgctgtgtctggt 3' | 58° C. | | | 0.5 µM | | | |
| Inner | G6PDNR-(SEQ ID NO:32) 5' ggacatgacaacttgggctt 3' | 58° C. | | | 0.5 µM | | | |
| | Factor V | | 0.025 | ng 0.01 | ng | 0.5 ng | 0.5 ng | 0.01 ng |
| Outer | FACT5FU-(SEQ ID NO:33) 5' ttgaaggaaaugccccatta 3' | 60° C. | | | 0.2 µM | | | |
| Outer | FACT5RU-(SEQ ID NO:34) | 60° C. | | | 0.2 µM | | | |

TABLE 1-continued

| Primer pair | Primer Target Gene / Primer sequence | Annealing Temperature used | Lower limit of detection of initial target DNA using Outer and Inner primers alone | | One tube nested Primer Concentration | Lower limit of detection of initial target DNA | | One tube nested PCR |
|---|---|---|---|---|---|---|---|---|
| | | | | | | Classical nested PCR Aliquots from primary PCR | | |
| | | | Outer | Inner | | 1 μl | 10 μl | |
| | 5' taattggtuccagcgaaagc 3' | | | | | | | |
| Inner | FACT5NF-(SEQ ID NO:35) 5' ggttacttcaaggacaaatacctgta 3' | 60° C. | | | 0.5 μM | | | |
| Inner | FACT5NR-(SEQ ID NO:36) 5' tcaggcaggaacaacacca 3' | 60° C. | | | 0.5 μM | | | |
| | Prothrombin | | | | | | | |
| Outer | PROTHFU-(SEQ ID NO:37) 5' cccaccccucutttgagat 3' | 60° C. | 0.5 ng(-) | 0.025 ng | 0.2 μM | | | |
| Outer | PROTHRU-(SEQ ID NO:38) 5' ggactcggguctctccgac 3' | 60° C. | | | 0.2 μM | | | |
| Inner | PROTHNF-(SEQ ID NO:39) 5' tctagaaacagttgcctggca 3' | 60° C. | | | 0.5 μM | | | |
| Inner | PROTHNR-(SEQ ID NO:40) 5' atagcactggagcattgagg 3' | 60° C. | | | 0.5 μM | — | 5 ng | 0.01 ng nested PCR |
| | SSBP (RT-PCR) | | | | | | | |
| Outer | SSBFU (SEQ ID NO:41) 5' ugucuugagacagguggaagg 3' | 58° C. | | | 0.2 μM | | | |
| Outer | SSBRU (SEQ ID NO:42) 5' uccuucuuucgucugguca 3' | 58° C. | | | 0.2 μM | ND | ND | 0.1 ng total RNA |

TABLE 1-continued

| Primer pair | Target Gene Primer sequence | Annealing Temperature used | Lower limit of detection of initial target DNA using Outer and Inner primers alone | | One tube nested Primer Concentration | Lower limit of detection of initial target DNA | |
|---|---|---|---|---|---|---|---|
| | | | Outer | Inner | | Classical nested PCR Aliquots from primary PCR 1 μl    10 μl | One tube nested PCR |
| Inner | SSBF (SEQ ID NO:43) 5' gcgatcagggatagtgaag 3' | 58° C. | | | 0.5 μM | | |
| Inner | SSBR (SEQ ID NO:44) 5' ttgcttgtcgcctcacatta 3' | 58° C. | | | 0.5 μM | | |

ND = not done,
1TN = one tube nested,
Class = classical,
− = no amplification visualized
Myc: different temperatures were used for the one tube PCR and the classical nested PCR

What is claimed is:

1. A method for amplifying a target nucleic acid sequence present in a template nucleic acid molecule, said method comprising:
   (a) assembling an amplification reaction mixture comprising:
      (1) the template,
      (2) an outer primer pair each of which comprises a sequence with sufficient complementarity to a portion of the template to anneal to the template in an amplification reaction, wherein at least one member of the outer primer pair contains at least one exo-sample nucleotide;
      (3) at least one inner primer that comprises a sequence with sufficient complementarity to a portion of the template to anneal to the template in an amplification reaction, wherein the portion of the template to which the inner primer anneals is between the portions of the template to which the outer primers anneal; and
      (4) an agent capable of degrading an exo-sample nucleotide; and
   (b) conducting an amplification reaction using the amplification reaction mixture;
   wherein the agent capable of degrading an exo-sample nucleotide is present in the reaction mixture prior to amplification with the outer primer pair.

2. The method of claim 1, wherein degrading an exo-sample nucleotide in an outer primer results in degradation of the outer primer.

3. The method of claim 1, wherein the agent is an enzyme.

4. The method of claim 3, wherein the enzyme is a glycosylase.

5. The method of claim 4, wherein the glycosylase is a DNA glycosylase.

6. The method of claim 4, wherein the glycosylase is selected from the group consisting of uracil-DNA glycosylase, UNGs, UNG1, TAG, alkA, MAG, MAG1, N-methylpurine glycosylase, EndoIII, EndoVIII, EndoIX, NTG1, NTH, hydroxy-methyl-DNA glycosylase, formyluracil-DNA glycosylase; 2,6-dihydroxy-5N-formamiodopyrimidine DNA glycosylase, OGG1, OGG2, S3, PDG, and 5-methyl-cytosine-DNA glycosylase.

7. The method of claim 1, wherein the exo-sample nucleotide is a nucleotide selected from the group consisting of deoxyuridine, bromodeoxyuridine, 7-methylguanine, 5,6-dihdro-5,6-dihydroxydeoxythimidin- e, 3-methyldeoxadenosine, inosine, 5-bromo-deoxycitidine, 5-methyldeoxycitidine, 5-bromodeoxyuridine, O-6-methyl-deoxyguanosine, 5-iododeoxyuridine, 8-oxo-deoxyguanine, ethanoadenine, and 5,6-dihydrouracil.

8. The method of claim 1, wherein at least one of the outer primers is from about 6 nucleotides to about 1000 nucleotides in length.

9. The method of claim 1, wherein at least one of the inner primers is from about 6 nucleotides to about 1000 nucleotides in length.

10. The method of claim 1, wherein the target nucleic acid sequence is amplified by polymerase chain reaction.

11. The method of claim 1, wherein the target nucleic acid sequence is amplified by two or more polymerase chain reactions.

12. The method of claim 11, wherein the polymerase chain reaction is a reverse-transcriptase polymerase chain reaction or a rapid cycle capillary polymerase chain reaction.

* * * * *

SEQUENCE LISTING

<160> NUMBER OF SEQ ID NOS: 44

<210> SEQ ID NO 1
<211> LENGTH: 20
<212> TYPE: DNA
<213> ORGANISM: Artificial Sequence
<220> FEATURE:
<223> OTHER INFORMATION: Oligonucleotide primer
<220> FEATURE:
<221> NAME/KEY: misc_feature
<222> LOCATION: (1)..(2)
<223> OTHER INFORMATION: deoxyuridine
<220> FEATURE:
<221> NAME/KEY: misc_feature
<222> LOCATION: (5)..(7)
<223> OTHER INFORMATION: deoxyuridine
<220> FEATURE:
<221> NAME/KEY: misc_feature
<222> LOCATION: (12)..(12)
<223> OTHER INFORMATION: deoxyuridine
<220> FEATURE:
<221> NAME/KEY: misc_feature
<222> LOCATION: (19)..(19)
<223> OTHER INFORMATION: deoxyuridine

<400> SEQUENCE: 1
nnccnnngca cngaaagcng                                           20

<210> SEQ ID NO 2
<211> LENGTH: 20
<212> TYPE: DNA
<213> ORGANISM: Artificial Sequence
<220> FEATURE:
<223> OTHER INFORMATION: Oligonucleotide primer
<220> FEATURE:
<221> NAME/KEY: misc_feature
<222> LOCATION: (4)..(4)
<223> OTHER INFORMATION: deoxyuridine
<220> FEATURE:
<221> NAME/KEY: misc_feature
<222> LOCATION: (7)..(7)
<223> OTHER INFORMATION: deoxyuridine
<220> FEATURE:
<221> NAME/KEY: misc_feature
<222> LOCATION: (10)..(10)
<223> OTHER INFORMATION: deoxyuridine
<220> FEATURE:
<221> NAME/KEY: misc_feature
<222> LOCATION: (14)..(15)
<223> OTHER INFORMATION: deoxyuridine
<220> FEATURE:
<221> NAME/KEY: misc_feature
<222> LOCATION: (17)..(18)
<223> OTHER INFORMATION: deoxyuridine

<400> SEQUENCE: 2
agcnggngcn ccanncnnga                                           20

<210> SEQ ID NO 3
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 3
gagaatccca gaatgcgaaa                                           20

<210> SEQ ID NO 4
<211> LENGTH: 20

```
<212> TYPE: DNA
<213> ORGANISM: Artificial Sequence
<220> FEATURE:
<223> OTHER INFORMATION: Oligonucleotide primer

<400> SEQUENCE: 4
caattcttcg gcagcatctt                                          20

<210> SEQ ID NO 5
<211> LENGTH: 20
<212> TYPE: DNA
<213> ORGANISM: Artificial Sequence
<220> FEATURE:
<223> OTHER INFORMATION: Oligonucleotide primer
<220> FEATURE:
<221> NAME/KEY: misc_feature
<222> LOCATION: (10)..(10)
<223> OTHER INFORMATION: deoxyuridine
<220> FEATURE:
<221> NAME/KEY: misc_feature
<222> LOCATION: (17)..(17)
<223> OTHER INFORMATION: deoxyuridine

<400> SEQUENCE: 5
aaggcaacgn ccagganaga                                          20

<210> SEQ ID NO 6
<211> LENGTH: 19
<212> TYPE: DNA
<213> ORGANISM: Artificial Sequence
<220> FEATURE:
<223> OTHER INFORMATION: Oligonucleotide primer
<220> FEATURE:
<221> NAME/KEY: misc_feature
<222> LOCATION: (1)..(1)
<223> OTHER INFORMATION: deoxyuridine
<220> FEATURE:
<221> NAME/KEY: misc_feature
<222> LOCATION: (5)..(5)
<223> OTHER INFORMATION: deoxyuridine
<220> FEATURE:
<221> NAME/KEY: misc_feature
<222> LOCATION: (12)..(12)
<223> OTHER INFORMATION: deoxyuridine

<400> SEQUENCE: 6
ncgcngcaga gnaccgaag                                           19

<210> SEQ ID NO 7
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 7
catgaacgca ttcatcgtgt ggtc                                     24

<210> SEQ ID NO 8
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 8
ctgcgggaag caaactgcaa ttctt                                    25

<210> SEQ ID NO 9
```

```
<211> LENGTH: 20
<212> TYPE: DNA
<213> ORGANISM: Artificial Sequence
<220> FEATURE:
<223> OTHER INFORMATION: Oligonucleotide primer
<220> FEATURE:
<221> NAME/KEY: misc_feature
<222> LOCATION: (4)..(4)
<223> OTHER INFORMATION: deoxyuridine
<220> FEATURE:
<221> NAME/KEY: misc_feature
<222> LOCATION: (7)..(7)
<223> OTHER INFORMATION: deoxyuridine
<220> FEATURE:
<221> NAME/KEY: misc_feature
<222> LOCATION: (13)..(13)
<223> OTHER INFORMATION: deoxyuridine
<220> FEATURE:
<221> NAME/KEY: misc_feature
<222> LOCATION: (16)..(16)
<223> OTHER INFORMATION: deoxyuridine
<220> FEATURE:
<221> NAME/KEY: misc_feature
<222> LOCATION: (18)..(18)
<223> OTHER INFORMATION: deoxyuridine

<400> SEQUENCE: 9
gccnccnaag acngcngngg                                             20

<210> SEQ ID NO 10
<211> LENGTH: 20
<212> TYPE: DNA
<213> ORGANISM: Artificial Sequence
<220> FEATURE:
<223> OTHER INFORMATION: Oligonucleotide primer
<220> FEATURE:
<221> NAME/KEY: misc_feature
<222> LOCATION: (1)..(1)
<223> OTHER INFORMATION: deoxyuridine
<220> FEATURE:
<221> NAME/KEY: misc_feature
<222> LOCATION: (3)..(5)
<223> OTHER INFORMATION: deoxyuridine
<220> FEATURE:
<221> NAME/KEY: misc_feature
<222> LOCATION: (13)..(14)
<223> OTHER INFORMATION: deoxyuridine
<220> FEATURE:
<221> NAME/KEY: misc_feature
<222> LOCATION: (17)..(17)
<223> OTHER INFORMATION: deoxyuridine

<400> SEQUENCE: 10
ncnnnggccc agnngcnagt                                             20

<210> SEQ ID NO 11
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 11
gaaattacac acataggtgg cact                                        24

<210> SEQ ID NO 12
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 12
```
ccctgatgaa gaacttgtat ctc                                    23

<210> SEQ ID NO 13
<211> LENGTH: 20
<212> TYPE: DNA
<213> ORGANISM: Artificial Sequence
<220> FEATURE:
<223> OTHER INFORMATION: Oligonucleotide primer
<220> FEATURE:
<221> NAME/KEY: misc_feature
<222> LOCATION: (5)..(6)
<223> OTHER INFORMATION: deoxyuridine
<220> FEATURE:
<221> NAME/KEY: misc_feature
<222> LOCATION: (12)..(13)
<223> OTHER INFORMATION: deoxyuridine
<220> FEATURE:
<221> NAME/KEY: misc_feature
<222> LOCATION: (15)..(15)
<223> OTHER INFORMATION: deoxyuridine
<220> FEATURE:
<221> NAME/KEY: misc_feature
<222> LOCATION: (19)..(19)
<223> OTHER INFORMATION: deoxyuridine

<400> SEQUENCE: 13
gccannaccg gnncnccana                                        20

<210> SEQ ID NO 14
<211> LENGTH: 20
<212> TYPE: DNA
<213> ORGANISM: Artificial Sequence
<220> FEATURE:
<223> OTHER INFORMATION: Oligonucleotide primer
<220> FEATURE:
<221> NAME/KEY: misc_feature
<222> LOCATION: (5)..(5)
<223> OTHER INFORMATION: deoxyuridine
<220> FEATURE:
<221> NAME/KEY: misc_feature
<222> LOCATION: (9)..(9)
<223> OTHER INFORMATION: deoxyuridine
<220> FEATURE:
<221> NAME/KEY: misc_feature
<222> LOCATION: (11)..(11)
<223> OTHER INFORMATION: deoxyuridine
<220> FEATURE:
<221> NAME/KEY: misc_feature
<222> LOCATION: (14)..(14)
<223> OTHER INFORMATION: deoxyuridine
<220> FEATURE:
<221> NAME/KEY: misc_feature
<222> LOCATION: (18)..(20)
<223> OTHER INFORMATION: deoxyuridine

<400> SEQUENCE: 14
ccaancgcna ngcnggannn                                        20

<210> SEQ ID NO 15
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 15
tctttcttcg gaccttctgc                                        20

<210> SEQ ID NO 16
<211> LENGTH: 20
<212> TYPE: DNA

```
<213> ORGANISM: Artificial Sequence
<220> FEATURE:
<223> OTHER INFORMATION: Oligonucleotide primer

<400> SEQUENCE: 16
cgttcaggtt tgcgaaagta                                        20

<210> SEQ ID NO 17
<211> LENGTH: 20
<212> TYPE: DNA
<213> ORGANISM: Artificial Sequence
<220> FEATURE:
<223> OTHER INFORMATION: Oligonucleotide primer
<220> FEATURE:
<221> NAME/KEY: misc_feature
<222> LOCATION: (5)..(5)
<223> OTHER INFORMATION: deoxyuridine
<220> FEATURE:
<221> NAME/KEY: misc_feature
<222> LOCATION: (11)..(12)
<223> OTHER INFORMATION: deoxyuridine
<220> FEATURE:
<221> NAME/KEY: misc_feature
<222> LOCATION: (15)..(15)
<223> OTHER INFORMATION: deoxyuridine
<220> FEATURE:
<221> NAME/KEY: misc_feature
<222> LOCATION: (18)..(18)
<223> OTHER INFORMATION: deoxyuridine

<400> SEQUENCE: 17
caggngacag nncgngangc                                        20

<210> SEQ ID NO 18
<211> LENGTH: 20
<212> TYPE: DNA
<213> ORGANISM: Artificial Sequence
<220> FEATURE:
<223> OTHER INFORMATION: Oligonucleotide primer
<220> FEATURE:
<221> NAME/KEY: misc_feature
<222> LOCATION: (6)..(6)
<223> OTHER INFORMATION: deoxyuridine
<220> FEATURE:
<221> NAME/KEY: misc_feature
<222> LOCATION: (14)..(15)
<223> OTHER INFORMATION: deoxyuridine
<220> FEATURE:
<221> NAME/KEY: misc_feature
<222> LOCATION: (19)..(19)
<223> OTHER INFORMATION: deoxyuridine

<400> SEQUENCE: 18
cccacnggaa ggcnnaccnc                                        20

<210> SEQ ID NO 19
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 19
ggtatggatg aggagctgga                                        20

<210> SEQ ID NO 20
<211> LENGTH: 20
<212> TYPE: DNA
<213> ORGANISM: Artificial Sequence
<220> FEATURE:
<223> OTHER INFORMATION: Oligonucleotide primer
```

```
<400> SEQUENCE: 20
cttccacagc cctcgactaa                                               20

<210> SEQ ID NO 21
<211> LENGTH: 20
<212> TYPE: DNA
<213> ORGANISM: Artificial Sequence
<220> FEATURE:
<223> OTHER INFORMATION: Oligonucleotide primer
<220> FEATURE:
<221> NAME/KEY: misc_feature
<222> LOCATION: (8)..(8)
<223> OTHER INFORMATION: deoxyuridine
<220> FEATURE:
<221> NAME/KEY: misc_feature
<222> LOCATION: (14)..(14)
<223> OTHER INFORMATION: deoxyuridine

<400> SEQUENCE: 21
actggcancg tganggactc                                               20

<210> SEQ ID NO 22
<211> LENGTH: 20
<212> TYPE: DNA
<213> ORGANISM: Artificial Sequence
<220> FEATURE:
<223> OTHER INFORMATION: Oligonucleotide primer
<220> FEATURE:
<221> NAME/KEY: misc_feature
<222> LOCATION: (7)..(7)
<223> OTHER INFORMATION: deoxyuridine
<220> FEATURE:
<221> NAME/KEY: misc_feature
<222> LOCATION: (12)..(12)
<223> OTHER INFORMATION: deoxyuridine

<400> SEQUENCE: 22
taacccncat gncaggcaga                                               20

<210> SEQ ID NO 23
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 23
acccacactg tgcccatct                                                19

<210> SEQ ID NO 24
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 24
ggaaccgctc attgccaat                                                19

<210> SEQ ID NO 25
<211> LENGTH: 24
<212> TYPE: DNA
<213> ORGANISM: Artificial Sequence
<220> FEATURE:
<223> OTHER INFORMATION: Oligonucleotide primer
<220> FEATURE:
<221> NAME/KEY: misc_feature
<222> LOCATION: (6)..(6)
```

```
<223> OTHER INFORMATION: deoxyuridine
<220> FEATURE:
<221> NAME/KEY: misc_feature
<222> LOCATION: (14)..(14)
<223> OTHER INFORMATION: deoxyuridine
<220> FEATURE:
<221> NAME/KEY: misc_feature
<222> LOCATION: (18)..(18)
<223> OTHER INFORMATION: deoxyuridine

<400> SEQUENCE: 25
attgtntgca gcancaanaa catt                                              24

<210> SEQ ID NO 26
<211> LENGTH: 22
<212> TYPE: DNA
<213> ORGANISM: Artificial Sequence
<220> FEATURE:
<223> OTHER INFORMATION: Oligonucleotide primer
<220> FEATURE:
<221> NAME/KEY: misc_feature
<222> LOCATION: (7)..(7)
<223> OTHER INFORMATION: deoxyuridine
<220> FEATURE:
<221> NAME/KEY: misc_feature
<222> LOCATION: (16)..(16)
<223> OTHER INFORMATION: deoxyuridine

<400> SEQUENCE: 26
ctggaantac atgtgngcca ct                                                22

<210> SEQ ID NO 27
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 27
ttgaccaatt tgaaacagtg agtt                                              24

<210> SEQ ID NO 28
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 28
acccagccgt atgttttcta ataa                                              24

<210> SEQ ID NO 29
<211> LENGTH: 20
<212> TYPE: DNA
<213> ORGANISM: Artificial Sequence
<220> FEATURE:
<223> OTHER INFORMATION: Oligonucleotide primer
<220> FEATURE:
<221> NAME/KEY: misc_feature
<222> LOCATION: (7)..(7)
<223> OTHER INFORMATION: deoxyuridine
<220> FEATURE:
<221> NAME/KEY: misc_feature
<222> LOCATION: (19)..(19)
<223> OTHER INFORMATION: deoxyuridine

<400> SEQUENCE: 29
acgtgangca gaaccaccna                                                   20
```

```
<210> SEQ ID NO 30
<211> LENGTH: 20
<212> TYPE: DNA
<213> ORGANISM: Artificial Sequence
<220> FEATURE:
<223> OTHER INFORMATION: Oligonucleotide primer
<220> FEATURE:
<221> NAME/KEY: misc_feature
<222> LOCATION: (9)..(9)
<223> OTHER INFORMATION: deoxyuridine
<220> FEATURE:
<221> NAME/KEY: misc_feature
<222> LOCATION: (17)..(17)
<223> OTHER INFORMATION: deoxyuridine

<400> SEQUENCE: 30
gccttcccng gtcacanagt                                           20

<210> SEQ ID NO 31
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 31
ctgcagatgc tgtgtctggt                                           20

<210> SEQ ID NO 32
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 32
ggacatgaca acttgggctt                                           20

<210> SEQ ID NO 33
<211> LENGTH: 20
<212> TYPE: DNA
<213> ORGANISM: Artificial Sequence
<220> FEATURE:
<223> OTHER INFORMATION: Oligonucleotide primer
<220> FEATURE:
<221> NAME/KEY: misc_feature
<222> LOCATION: (11)..(11)
<223> OTHER INFORMATION: deoxyuridine

<400> SEQUENCE: 33
ttgaaggaaa ngccccatta                                           20

<210> SEQ ID NO 34
<211> LENGTH: 20
<212> TYPE: DNA
<213> ORGANISM: Artificial Sequence
<220> FEATURE:
<223> OTHER INFORMATION: Oligonucleotide primer
<220> FEATURE:
<221> NAME/KEY: misc_feature
<222> LOCATION: (9)..(9)
<223> OTHER INFORMATION: deoxyuridine

<400> SEQUENCE: 34
taattggtnc cagcgaaagc                                           20

<210> SEQ ID NO 35
<211> LENGTH: 27
<212> TYPE: DNA
```

```
<213> ORGANISM: Artificial Sequence
<220> FEATURE:
<223> OTHER INFORMATION: Oligonucleotide primer

<400> SEQUENCE: 35
ggttacttca aggacaaaat acctgta                                    27

<210> SEQ ID NO 36
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 36
tcaggcagga acaacacca                                             19

<210> SEQ ID NO 37
<211> LENGTH: 19
<212> TYPE: DNA
<213> ORGANISM: Artificial Sequence
<220> FEATURE:
<223> OTHER INFORMATION: Oligonucleotide primer
<220> FEATURE:
<221> NAME/KEY: misc_feature
<222> LOCATION: (10)..(10)
<223> OTHER INFORMATION: deoxyuridine

<400> SEQUENCE: 37
ccccaccccn ctttgagat                                             19

<210> SEQ ID NO 38
<211> LENGTH: 18
<212> TYPE: DNA
<213> ORGANISM: Artificial Sequence
<220> FEATURE:
<223> OTHER INFORMATION: Oligonucleotide primer
<220> FEATURE:
<221> NAME/KEY: misc_feature
<222> LOCATION: (10)..(10)
<223> OTHER INFORMATION: deoxyuridine

<400> SEQUENCE: 38
ggactcgggn ctctcgac                                              18

<210> SEQ ID NO 39
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 39
tctagaaaca gttgcctggc a                                          21

<210> SEQ ID NO 40
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 40
atagcactgg gagcattgag g                                          21

<210> SEQ ID NO 41
<211> LENGTH: 21
```

```
<212> TYPE: DNA
<213> ORGANISM: Artificial Sequence
<220> FEATURE:
<223> OTHER INFORMATION: Oligonucleotide primer
<220> FEATURE:
<221> NAME/KEY: misc_feature
<222> LOCATION: (1)..(1)
<223> OTHER INFORMATION: deoxyuridine
<220> FEATURE:
<221> NAME/KEY: misc_feature
<222> LOCATION: (3)..(3)
<223> OTHER INFORMATION: deoxyuridine
<220> FEATURE:
<221> NAME/KEY: misc_feature
<222> LOCATION: (5)..(6)
<223> OTHER INFORMATION: deoxyuridine
<220> FEATURE:
<221> NAME/KEY: misc_feature
<222> LOCATION: (15)..(15)
<223> OTHER INFORMATION: deoxyuridine

<400> SEQUENCE: 41
ngncnngaga caggnggaag g                                    21

<210> SEQ ID NO 42
<211> LENGTH: 21
<212> TYPE: DNA
<213> ORGANISM: Artificial Sequence
<220> FEATURE:
<223> OTHER INFORMATION: Oligonucleotide primer
<220> FEATURE:
<221> NAME/KEY: misc_feature
<222> LOCATION: (1)..(1)
<223> OTHER INFORMATION: deoxyuridine
<220> FEATURE:
<221> NAME/KEY: misc_feature
<222> LOCATION: (4)..(5)
<223> OTHER INFORMATION: deoxyuridine
<220> FEATURE:
<221> NAME/KEY: misc_feature
<222> LOCATION: (7)..(7)
<223> OTHER INFORMATION: deoxyuridine
<220> FEATURE:
<221> NAME/KEY: misc_feature
<222> LOCATION: (9)..(11)
<223> OTHER INFORMATION: deoxyuridine
<220> FEATURE:
<221> NAME/KEY: misc_feature
<222> LOCATION: (14)..(14)
<223> OTHER INFORMATION: deoxyuridine
<220> FEATURE:
<221> NAME/KEY: misc_feature
<222> LOCATION: (16)..(16)
<223> OTHER INFORMATION: deoxyuridine
<220> FEATURE:
<221> NAME/KEY: misc_feature
<222> LOCATION: (19)..(19)
<223> OTHER INFORMATION: deoxyuridine

<400> SEQUENCE: 42
nccnncncnn ncgncnggnc a                                    21

<210> SEQ ID NO 43
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 43
gcgatcaggg gatagtgaag                                      20

<210> SEQ ID NO 44
```

```
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 44
ttgcttgtcg cctcacatta                                          20
```